US006902915B2

(12) United States Patent
Tokuyama et al.

(10) Patent No.: US 6,902,915 B2
(45) Date of Patent: Jun. 7, 2005

(54) HEAT-STABLE D-AMINOACYLASE

(75) Inventors: Shinji Tokuyama, Shizuoka (JP); Akinobu Matsuyama, Ibaraki (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/361,509

(22) Filed: Feb. 7, 2003

(65) Prior Publication Data

US 2003/0157665 A1 Aug. 21, 2003

Related U.S. Application Data

(62) Division of application No. 09/921,156, filed on Aug. 2, 2001, now Pat. No. 6,596,528.

(30) Foreign Application Priority Data

Aug. 2, 2000 (JP) ........................................ 2000-234470

(51) Int. Cl.$^7$ .......................... C12P 13/06; C12P 13/08; C12P 13/12; C12P 13/22; C12N 9/78
(52) U.S. Cl. ...................... 435/106; 435/108; 435/113; 435/115; 435/116; 435/227; 435/228; 435/253.5
(58) Field of Search ................................ 435/106, 108, 435/113, 115, 116, 227, 228, 253.5

(56) References Cited

U.S. PATENT DOCUMENTS

| 5,206,162 A | 4/1993 | Tsai et al. .................... 435/228 |
| 5,916,774 A | 6/1999 | Tokuyama ................... 435/71.2 |
| 6,030,823 A | 2/2000 | Tokuyama ................... 435/227 |

FOREIGN PATENT DOCUMENTS

| EP | 0976828 A1 | 2/2000 |
| EP | 1 129 465 A1 | 8/2001 |
| JP | 55042534 | 3/1980 |
| JP | 10210976 | 8/1998 |

OTHER PUBLICATIONS

Kameda, Yukio et al., "Studies on Acylase Activity and Micro–organisms. XXVI.[1]) Purification and Properties of D–Acylase (N–Acyl–D–amino–acid Amidohydrolase) from AAA 6029 (*Pseudomonas* sp.)[2)]", Chem. Pharm. Bull., vol. 26, No. 9, pp. 2698–2704, (1978).

Moriguchi, Mitsuaki et al., "Production, Purification, and Characterization of D–Aminoacylase from *Alcaligenes xylosoxydans* subsp. *xylosoxydans* A–6", Biosci. Biotech. Biochem., vol. 57, No. 7, pp. 1149–1152, (1993).

Moriguchi, Mitsuaki et al., "Purification and Characterization of Novel N–Acyl–D–asparate Amidohydrolase from *Alcaligenes xylosoxydans* subsp. *xylosoxydans* A–6", Biosci. Biotech. Biochem., vol. 57, No. 7, pp. 1145–1148, (1993).

Sakai, Kenji et al., "Purification and Properties of D–Aminoacylase from *Alcaligenes denitrificans* subsp. *xylosoxydans* MI–4", Journal of Fermentation and Bioengineering, vol. 71, No. 2, pp. 79–82, (1991).

Sugie, Makiko and Suzuki, Hideo, "Purification and Properties of D–Aminoacylase of *Streptomyces olivaceus*", Agric. Biol. Chem., vol. 42, No. 1, pp. 107–113, (1978).

Tsai, Ying–Chieh et al., "Production and Purification of D–Aminoacylase from *Alcaligenes denitrificans* and Taxonomic Study of the Strain", Applied and Environmental Microbiology, vol. 54, No. 4, pp. 984–989, (1988).

Yang, Yunn–Bor et al., "Characterization of D–Aminoacylase from *Alcaligenes denitrificans* DA181", Biosci. Biotech. Biochem., vol. 56, No. 9, pp. 1392–1395, (1992).

Kim, Bongcheol et al., "Classification of thermophilic streptomycetes, including the description of *Streptomyces thermoalcalitolerans* sp. nov.", International Journal of Systematic Bacteriology, vol. 49, No. 1, pp. 7–17 (1999).

*Primary Examiner*—Elizabeth Slobodyansky
(74) *Attorney, Agent, or Firm*—Fish & Richardson P.C.

(57) ABSTRACT

The present invention provides a novel D-aminoacylase, as well as method for producing a D-amino acid using the same. In order to achieve the above objective, the present inventors have succeeded in purifying heat-stable D-aminoacylase from microorganisms belonging to the genus *Streptomyces* by combining various purification methods. Furthermore, the present inventors found that the purified heat-stable D-aminoacylase is useful in industrial production of D-amino acids. By utilizing the heat-stable D-aminoacylase, it is possible to readily and efficiently produce the corresponding D-amino acids from N-acetyl-DL-amino acids (for example, N-acetyl-DL-methionine, N-acetyl-DL-valine, N-acetyl-DL-tryptophan, N-acetyl-DL-phenylalanine, N-acetyl-DL-alanine, N-acetyl-DL-leucine, and so on).

11 Claims, 9 Drawing Sheets

Heat tolerance of D-aminoacylase

Effect of temperature for enzymatic activity of D-aminoacylase

HEAT-STABLE D-AMINOACYLASE

CROSS REFERENCE TO RELATED APPLICATIONS

This application is a divisional of U.S. patent application Ser. No. 09/921,156, filed Aug. 2, 2001 now U.S. Pat. No. 6,596,528, which claims priority under 35 U.S.C. 119 to Japanese Patent Application No. 2002/234470, filed Aug. 2, 2000.

TECHNICAL FIELD

The present invention relates to a novel D-aminoacylase, as well as methods for producing D-amino acids using the same.

BACKGROUND

Enzymes have excellent catalytic functions with substrate specificity, reaction specificity, and stereospecificity. Stereospecificity of enzymes, with some exceptions, are nearly absolute.

Recent precise research has increased the importance of optically active substances for use in drugs, pesticides, feeds, and perfumes. Optical isomers sometimes have quite different biological activities; for example, D(R)-form thalidomide has no teratogenic activity, while its L(S)-form shows strong teratogenicity. Thus, the practical use of the thalidomide racemate caused the drug injury incidents by thalidomide. Furthermore, if one enantiomer shows an effective biological activity, the other enantiomer sometimes not only has no activity but moreover competitively inhibits the activity of the effective enantiomer. As a result, the biological activity of the racemate is reduced to half or less of the activity of the effective enantiomer. Accordingly, it is industrially important to obtain (synthesize or optically resolve) optically pure enantiomers. For this objective, an effective procedure has been used widely to optically resolve racemates synthesized. In particular, enzymatic optical resolution has drawn attention because it does not produce by-products and a bulk of liquid waste.

Generally, L-amino acids are widely and largely utilized in seasonings, food and feed additives, and infusions, and are thus very highly demanded. L-amino acids have been produced mainly by direct fermentation using microorganisms. Optical resolution in which N-acyl-DL-amino acids are hydrolyzed with L-aminoacylases is also a known method for producing L-amino acids. It has been utilized to industrially produce L-amino acids that are difficult to produce by fermentation. These L-aminoacylases are widely found in animals, plants, and microorganisms. They have been purified from various organisms, and their properties have been clarified. N-terminal amino acids of many proteins are considered to be N-acetylated in vivo. L-aminoacylases presumably regenerate the N-acetyl-amino acids produced by decomposition of proteins to amino acids. Among L-aminoacylases, an acylase that acts on N-acyl-L-glutamic acid is reported to be involved in arginine biosynthesis (Fruh, H., Leisinger, T.: J. Gen. Microb. 125, pp1 (1981)).

In contrast, D-amino acids have not been a subject of interest for a long time because they are nonprotein amino acids. D-amino acids were known to naturally occur only in small cyclic peptides, peptidoglycan of bacterial cell walls, and peptide antibiotics. However, D-amino acids have been demonstrated to be constituents of neuro-peptides and to exist as binding forms in tooth enamel, the lens, and cerebral proteins, resulting in investigation of physiological significance and enzymatic synthesis of D-amino acids.

At present, DL-amino acids have been optically resolved by physicochemical, chemical, and enzymatic methods. The enzymatic methods are the most convenient and industrially applicable for, for example, continuously producing L-methionine from N-acetyl-DL-methionine using a bioreactor on which L-aminoacylase is immobilized. D-amino acids may also be produced using hydantoinase. The method involves a two-step enzymatic reaction. The first reaction uses D-specific hydantoinase to convert D,L-5-substituted-hydantoin, which is synthesized at low cost from aldehyde analogues, to a D-carbamyl derivative. The second reaction uses D-amino acid carbamylase. Moreover, a method is known in which D-aminoacylase hydrolyzes N-acetyl-DL-amino acids to produce D-amino acids (Sugie, M. and Suzuki, H.: Argric. Biol. Chem. 44, pp1089 (1980), Tsai, Y. C., Lin, C. S., Tseng, T. H., Lee, H. and Wang, Y. J.: J. Enzyme Microb. Technol. 14, pp384 (1992)). Thus, D-aminoacylases are important for production of D-amino acids. However, their physiologic importance and structural functions and so on remain to be resolved.

D-aminoacylase was first reported to be found in Pseudomonas sp. KT83 isolated from soil by Kameda et al. in 1952 (Kameda, Y., Toyoura, H., Kimura, Y. and Yasuda, Y.: Nature 170, pp888 (1952)). This enzyme hydrolyzed N-benzoyl derivatives of D-phenylalanine, D-tyrosine, and D-alanine. Thereafter, D-aminoacylases derived from microorganisms were reported as follows:

Genus *Pseudomonas* (Kubo, K., Ishikura, T., and Fukagawa, Y.: J. Antibiot. 43, pp550 (1980); Kubo, K., Ishikura, T. and Fukagawa, Y.: J. Antibiot. 43, pp556 (1980); Kameda, Y., Hase, T., Kanatomo, S. and Kita, Y.: Chem. Pharm. Bull. 26, pp2698 (1978); Kubo, K., Ishikura, T. and Fukagawa, Y.: J. Antibiot. 43, pp543 (1980));

Genus *Streptomyces* (Sugie, M. and Suzuki, H.: Argric. Biol. Chem. 42, pp107 (1978); Sugie, M. and Suzuki, H.: Argric. Biol. Chem. 44, pp1089 (1980));

Genus *Alcaligenes* (Tsai, Y. C., Tseng, C. P., Hsiao, K. M. and Chen, L. Y.: Appl. Environ. Microbiol. 54, pp984 (1988); Yang, Y. B., Hsiao, K. M., Li, H., Yano, Y., Tsugita, A. and Tsai, Y. C.: Biosci. Biotech. Biochem. 56, pp1392 (1992); Yang, Y. B., Lin, C. S., Tseng, C. P., Wang, Y. J. and Tsai, Y. C.: Appl. Environ. Microbiol. 57, pp2767 (1991); Tsai, Y. C., Lin, C. S., Tseng, T. H., Lee, H. and Wang: Microb. Technol. 14, pp384 (1992); Moriguchi, M. and Ideta, K.: Appl. Environ. Microbiol. 54, pp2767 (1988); Sakai, K., Imamura, K., Sonoda, Y., Kido, H. and Moriguchi, M.: FEBS, 289, pp44 (1991); Sakai, K., Obata, T., Ideta, K. and Moriguchi, M.: J. Ferment. Bioeng. 71, pp79 (1991); Sakai, K., Oshima, K. and Moriguchi, M.: Appl. Environ. Microbiol. 57, pp2540 (1991); Moriguchi, M., Sakai, K., Katsuno, Y., Maki, T. and Wakayama, M.: Biosci. Biotech. Biochem., 57, pp1145 (1993); Wakayama, M., Ashika, T., Miyamoto, Y., Yoshikawa, T., Sonoda, Y., Sakai, K. and Moriguchi, M.: J. Biochem. 118, pp204 (1995)); Moriguchi, M., Sakai, K., Miyamoto, Y. and Wakayama, M.: Biosci. Biotech. Biochem., 57, pp1149 (1993));

Genus *Amycolatopsis* (Japanese Patent Application No. Hei 9-206288);

Genus *Sebekia* (Japanese Patent Application No. Hei 10-089246); and fungus (Japanese Patent Application No. Hei 10-228636).

Tsai et al. and Moriguchi et al. also clarified the characteristics of D-aminoacylase derived from microorganisms belonging to the genera *Alcaligenes* and *Pseudomonas* and the amino acid and nucleotide sequences of the enzymes.

Moriguchi et al. found, by using different inducers, three types of D-aminoacylases in microorganisms belonging to the genera *Alcaligenes* and *Pseudomonas* (Wakayama, M., Katsumo, Y., Hayashi, S., Miyamoto, Y., Sakai, K. and Moriguchi, M.: Biosci. Biotech. Biochem. 59, pp2115 (1995)).

Furthermore, Moriguchi et al. determined the nucleotide sequences of these D-aminoacylases derived from a microorganism belonging to the genus *Alcaligenes* and compared them with L-aminoacylases derived from *Bacillus stereothermophilus*, human, and pig. The results demonstrated that these D-aminoacylases have a low homology with L-aminoacylases (Wakayama, M., Katsuno, Y., Hayashi, S., Miyamoto, Y., Sakai, K. and Moriguchi, M.: Biosci. Biotech. Biochem., 59, pp2115 (1995)).

As to *Actinomycetes*, Sugie et al. reported D-aminoacylase of a microorganism belonging to the genus *Streptomyces* (Sugie, M. and Suzuki, H.: Argric. Biol. Chem. 42, pp107 (1978), Sugie, M. and Suzuki, H.: Argric. Biol. Chem. 44, pp1089 (1980)). However, the enzyme has not yet been purified, and its characteristics have not been well clarified.

The thermal stability of any of these known D-aminoacylases above are below 50° C., and the optimal temperature is below 50° C. No D-aminoacylases with higher thermal stability is presently known. It is economically advantageous to use heat-stable D-aminoacylases, since durability of the enzyme rises with thermal stability. Moreover, application of heat-stable D-aminoacylases in the production of D-amino acid possesses economic merit as well, since it is possible to set the reaction temperature high enough to elevate the concentration of the substrate and such due to the higher solubility.

SUMMARY

The object of the present invention is to isolate a heat-stable D-aminoacylase. Another object of the present invention is to provide methods for producing D-amino acids using the heat-stable D-aminoacylase.

In order to achieve the objectives above, the present inventors have succeeded in purifying heat-stable D-aminoacylase from microorganisms belonging to the genus *Streptomyces* by combining various purification methods. Furthermore, the present inventors found out that the purified heat-stable D-aminoacylase is useful in industrial production of D-amino acids.

Thus, the present invention relates to the heat-stable D-aminoacylase below, as well as the use of the same. More specifically, the invention provides:

(1) A heat-stable D-aminoacylase having the following physicochemical properties of (a) to (c) below:
   (a) action: the enzyme acts on N-acyl-D-amino acids to produce the corresponding D-amino acid;
   (b) thermal stability: the enzyme is stable at 55° C. when heated at pH 7.5 for 60 minutes, but is inactivated at 70° C. or more under the same condition;
   (c) optimal temperature: under the condition of pH 7.5, temperature around 60° C. is suited.

(2) The heat-stable D-aminoacylase of (1), which has also the following physicochemical properties of (d) to (g) below.
   (d) molecular weight: a molecular weight of approximately 40,000 daltons measured by SDS-polyacrylamide gel electrophoresis;
   (e) substrate specificity: the enzyme efficiently catalyzes the reaction with N-acetyl-D-methionine, N-acetyl-D-tryptophan and N-acetyl-D-phenylalanine, and catalyzes the reaction with N-acetyl-D-valine, N-acetyl-D-alanine and N-acetyl-D-leucine, but has substantially no catalytic activity for N-acetyl-L-methionine, N-acetyl-L-valine, or N-acetyl-L-phenylalanine;
   (f) optimal pH: a pH about 7.0 is suited, when acted at 30° C. for 60 minutes;
   (g) effect of metal ion: the activity is accelerated with 1 mM Co2+, but is markedly inhibited with 1 mM Cu2+.

(3) The heat-stable D-aminoacylase of (1) or (2), which is derived from microorganisms belonging to the genus *Streptomyces*.

(4) A heat-stable D-aminoacylase derived from *Streptomyces thermonitrificans* CS5-9, deposited under the accession No. FERM BP-7678.

(5) *Streptomyces thermonitrificans* CS5-9, deposited under the accession No. FERM BP-7678.

(6) A DNA encoding the heat-stable D-aminoacylase of any of (1) to (4).

(7) A method for producing the heat-stable D-aminoacylase of any of (1) to (4), said method comprising culturing a microorganism producing the heat-stable D-aminoacylase of any of (1) to (4) and recovering the microorganism or the culture supernatant.

(8) A method for producing a D-amino acid, wherein said method comprises contacting the heat-stable D-aminoacylase of any of (1) to (4) with N-acyl-DL-amino acid.

(9) A method for producing a D-amino acid, wherein said method comprises contacting a microorganism producing the heat-stable D-aminoacylase of any of (1) to (4), or a processed product thereof, with N-acyl-DL-amino acid.

(10) The method of (8) or (9), wherein the N-acyl-DL-amino acid is N-acetyl-DL-methionine, N-acetyl-DL-valine, N-acetyl-DL-tryptophan, N-acetyl-DL-asparagine, N-acetyl-DL-phenylalanine, N-acetyl-DL-alanine, or N-acetyl-DL-leucine.

gel volume: 50 ml equilibration and washing: 50 mM phosphate buffer 250 ml elution: 250 ml of buffer with a linear gradient of 0 M to 0.5 M NaCl, each fraction contained 5 ml solution.

Figure 4:
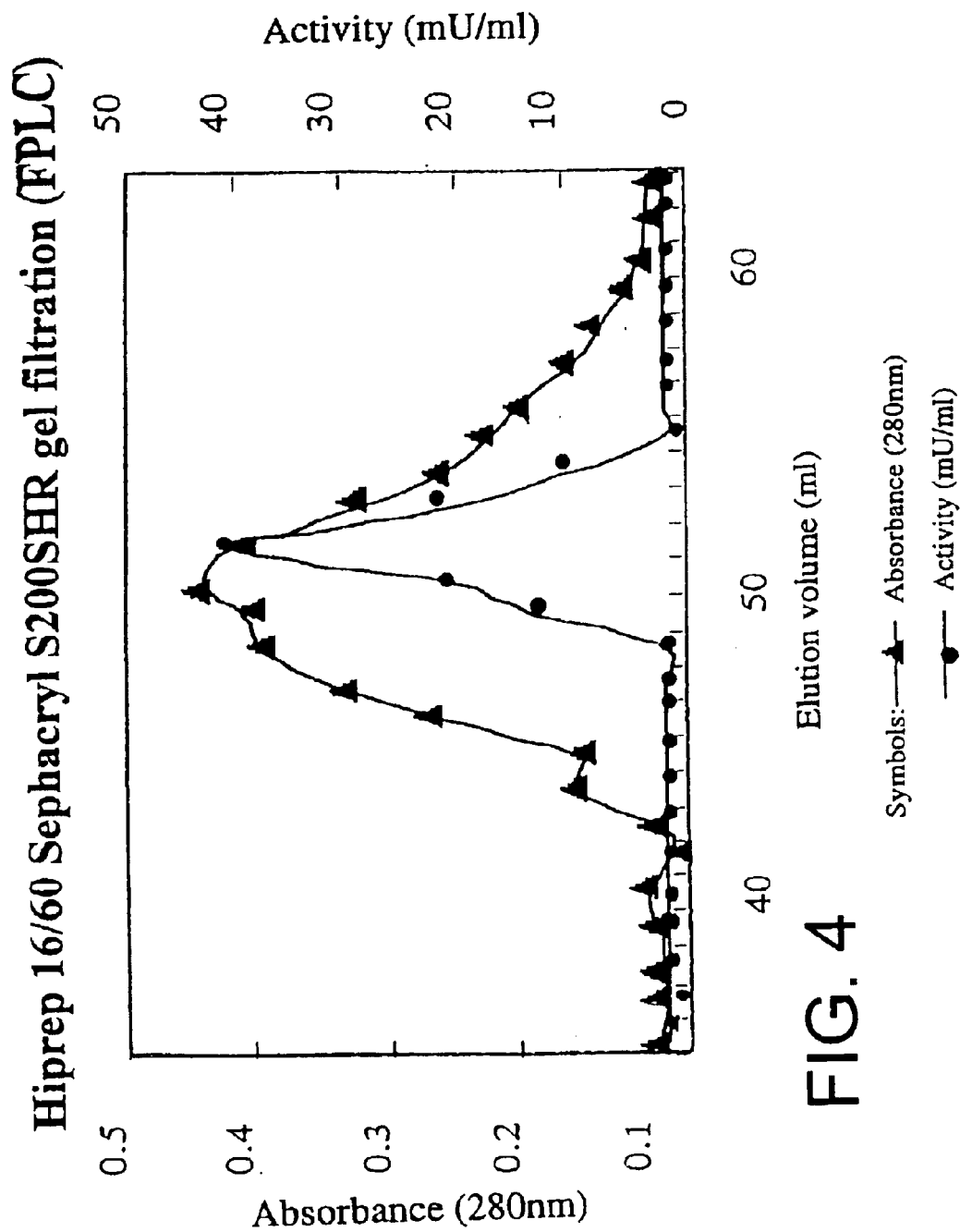
Figure 5:
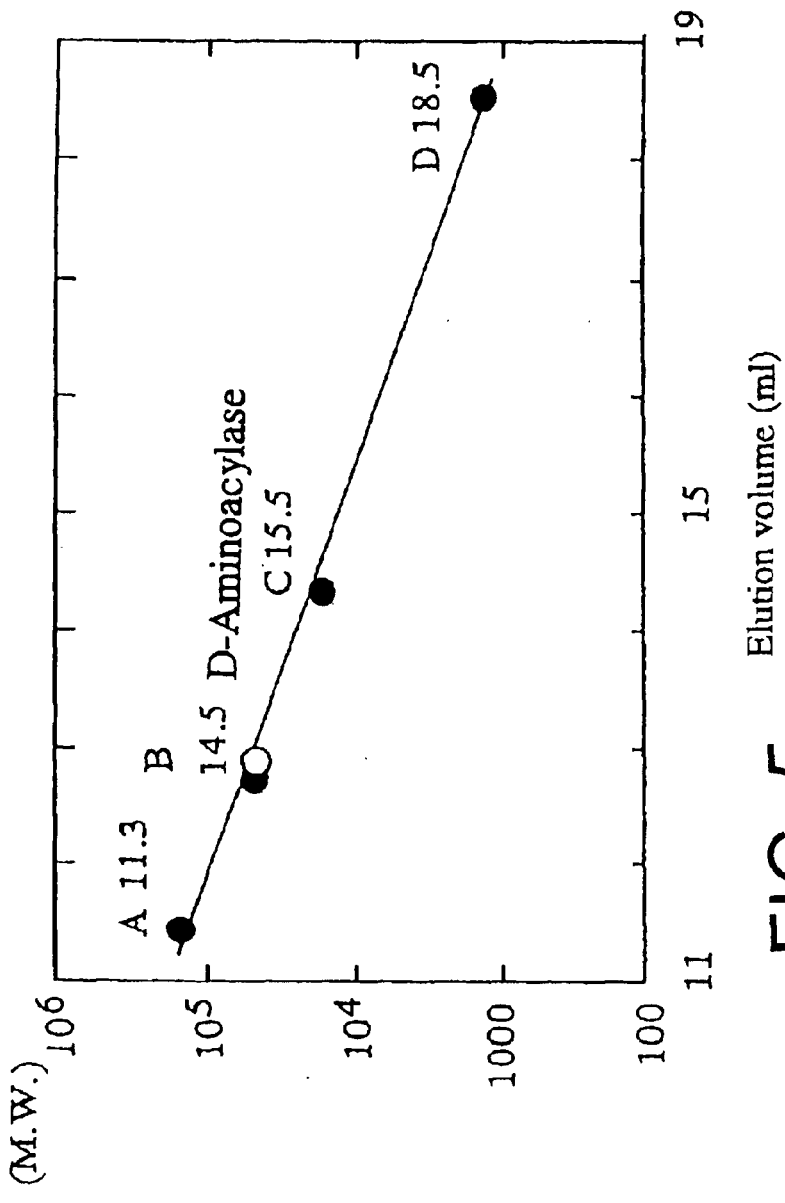

FIG. 4 illustrates purification of the D-aminoacylase of the present invention by gel filtration using HiPrep 16/60 Sephacryl S200 HR. The triangles denote the absorbance (at 280 nm), the circles the activity (by mU/ml). Additional parameters include:

gel volume: 320 ml equilibration and washing: 640 ml of 50 mM phosphate buffer containing 0.15 M NaCl elution: the same buffer as above. Flow rate 0.5 ml/min FIG. 5 illustrates the result of measurement of the molecular weight of the D-aminoacylase of the present invention by gel filtration. The letters in the figure denote the following: A: gamma globulin (158,000); B: ovalbumin (44,000); C: myoglobin (17,000); D: vitamin B-12 (1,350). The circle denotes the position where the D-aminoacylase of the present invention was eluted and its molecular weight.

Figure 6:
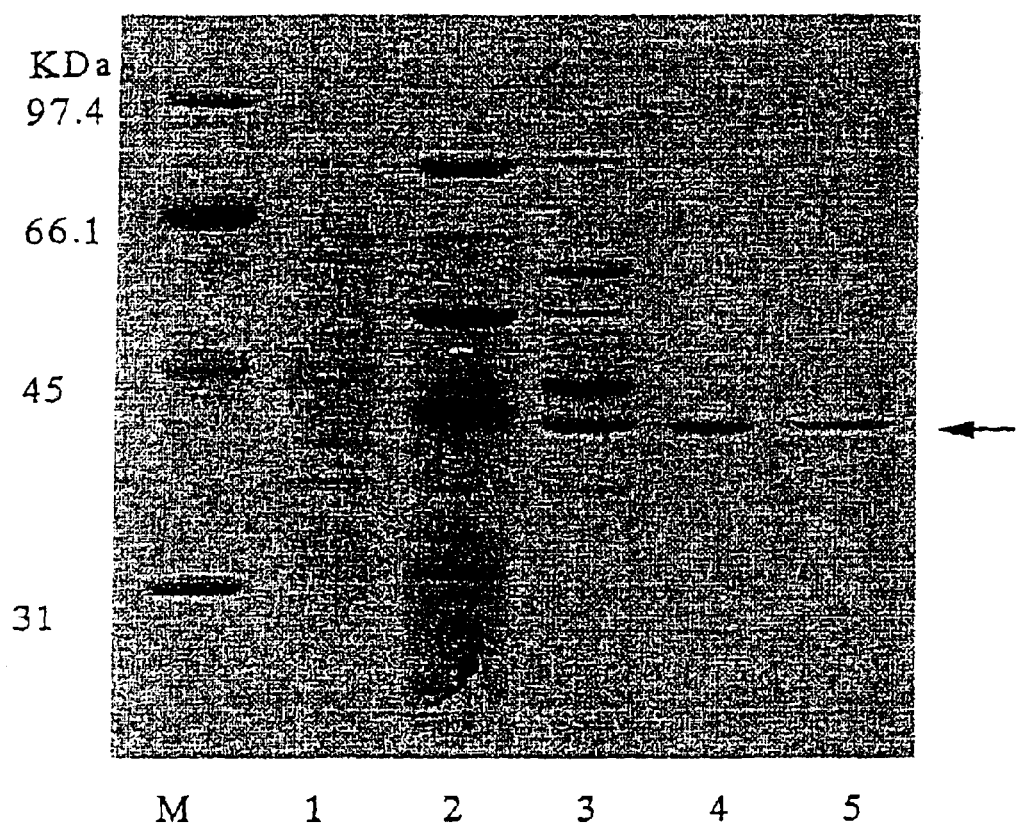

FIG. 6 illustrates the result of measurement of the molecular weight of the D-aminoacylase of the present invention by SDS-PAGE method. Phosphorylase B (97.4 K), serum albumin (66.1 K), ovalbumin (45 K), and carbonic anhydrase (31 K) were used as the molecular weight marker. The concentration of separation gel was 10%. M: molecular weight marker; 1: crude enzyme solution; 2: Butyl-Toyopearl chromatography (first time); 3: DEAE Toyopearl chromatography; 4: hiprep 10/60 Sephacryl S200 gel filtration; 5: MonoQ HR 5/5.

Figure 7:
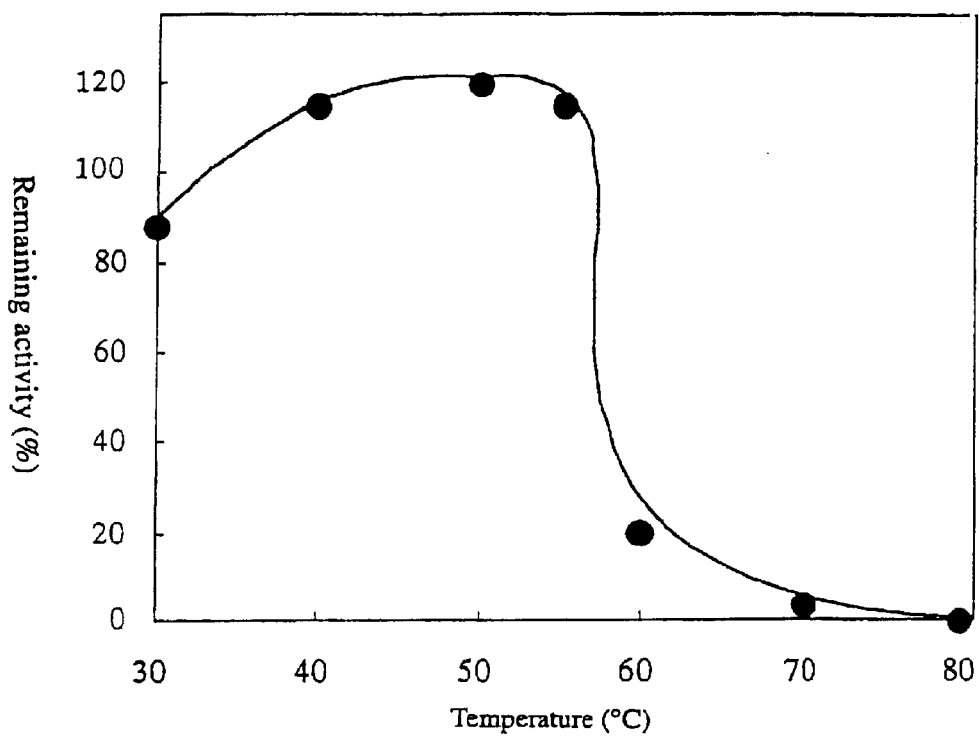

FIG. 7 shows the thermal stability of the D-aminoacylase of the present invention. The standard reaction mixture solution without the substrate, N-acetyl-D-methionine, was preincubated for 30 minutes at each temperature, and was cooled thereafter to 0° C. immediately. Then, N-acetyl-D-methionine was added and the enzyme reaction was carried on for 60 minutes. The remaining activity was calculated taking the activity of the untreated reaction as 100%.

Figure 8:
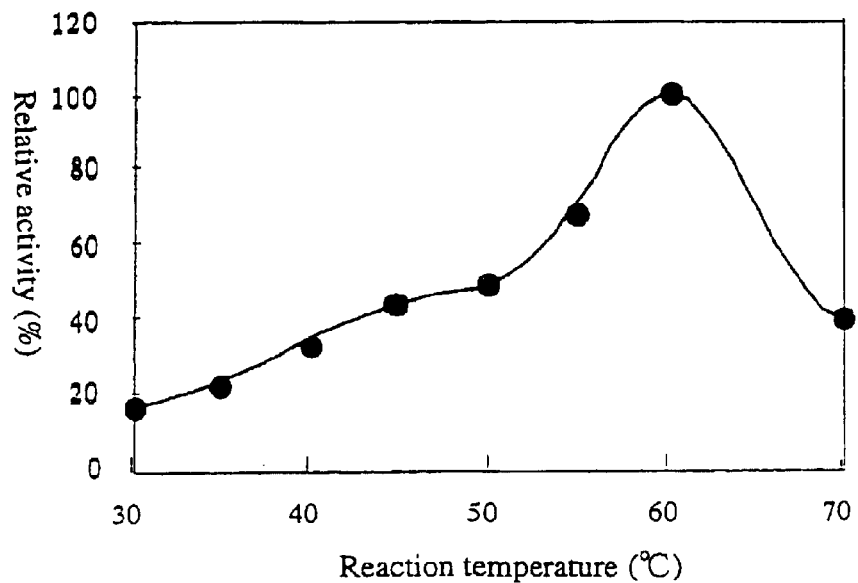

FIG. 8 shows the optimal reaction temperature of the D-aminoacylase of the present invention. The standard reaction mixture solution without the enzyme was warmed to 30° C. before the enzyme reaction, and 15 minutes of enzyme reaction was measured.

Figure 9:
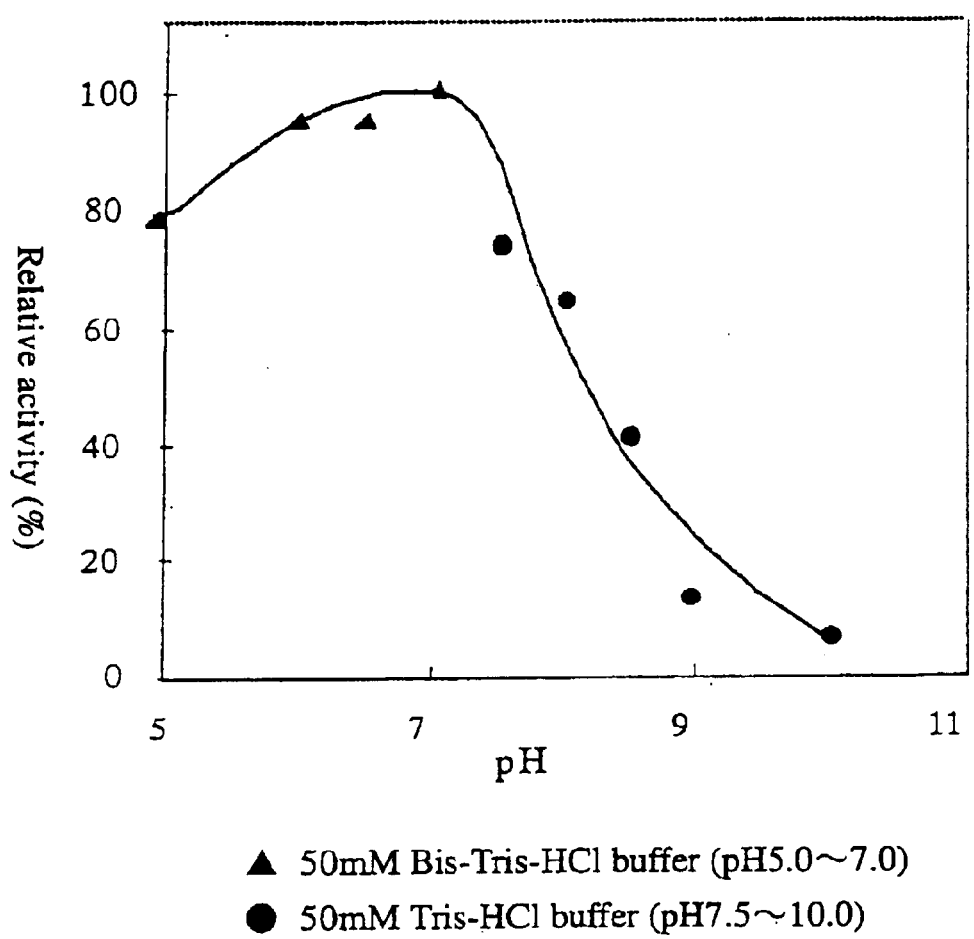

FIG. 9 shows the optimal reaction pH of the D-aminoacylase of the present invention. The triangles in the figure denote results with Bis-Tris-HCl buffer (pH 5.0 to 7.0), and the circles with 50 mM Tris-HCl buffer (pH 7.5 to 10.0).

Figure 10:
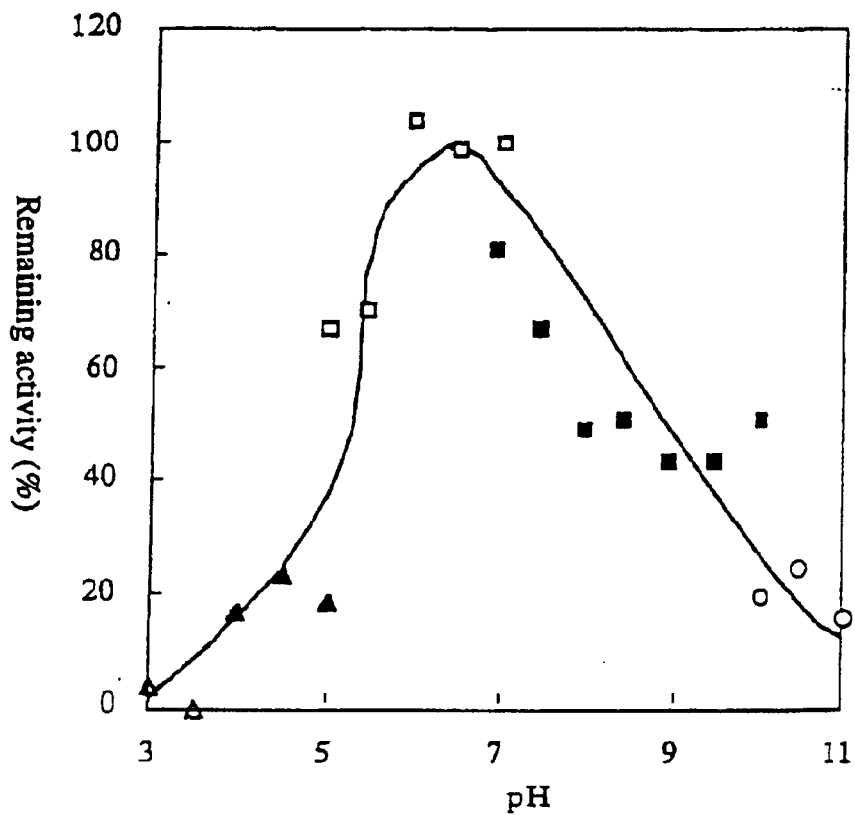

FIG. 10 shows the results of pH stability or the D-aminoacylase of the present invention. The enzyme was allowed to stand still for 20 minutes at each pH, at 4° C. Then, the activity was measured with standard reaction solution composition (pH 7.5) at 30° C. for 60 minutes. The remaining activity was calculated, taking the activity of the reaction at pH 7.0 as 100%. 50 mM buffer of the following were used: open triangle, citrate-NaOH (pH 3.0, 3.5); filled triangle, acetate-NaOH (pH 4.0 to 5.0); open box, Bis-Tris-HCl (pH 5.0 to 7.0); filled box, Tris-HCl (pH 7.0 to 10.0); open circle, Borate-NaOH (pH 10.0 to 11.0).

DETAILED DESCRIPTION

The present invention relates to heat-stable D-aminoacylase. The "D-aminoacylase" of the present invention refers to enzymes that catalyze the production of organic acids and D-amino acids from N-acyl-D-amino acid. The D-aminoacylase of the present invention has the physicochemical properties of (a) to (c) below.

(a) action: the enzyme acts on N-acyl-D-amino acids to produce the corresponding D-amino acid;

(b) thermal stability: the enzyme is stable at 55° C. when heated at pH 7.5 for 60 minutes, but is inactivated at higher temperature than 70° C. under the same condition; and (c) optimal temperature: under the condition of pH 7.5, temperature around 60° C. is suited.

The D-aminoacylase of the present invention preferably has also the physicochemical properties of (d) to (g) below.

(d) molecular weight: a molecular weight of approximately 40,000 daltons measured by SDS-polyacrylamide gel electrophoresis.

(e) substrate specificity: the enzyme efficiently catalyzes the reaction with N-acetyl-D-methionine, N-acetyl-D-tryptophan and N-acetyl-D-phenylalanine, and catalyzes the reaction with N-acetyl-D-valine, N-acetyl-D-alanine and N-acetyl-D-leucine, but has substantially no catalytic activity for N-acetyl-L-methionine, N-acetyl-L-valine, or N-acetyl-L-phenylalanine.

(f) optimal pH: a pH about 7.0 is suited, when acted at 30° C. for 60 minutes.

(g) effect of metal ion: the activity is accelerated with 1 mM $Co^{2+}$, but is markedly inhibited with 1 mM $Cu^{2+}$.

The activity of the D-aminoacylase of the present invention can be tested by the following procedure. For example, an enzyme solution (100 $\mu$l) is mixed and incubated with 50 mM Tris-HCl (pH 7.5) buffer (total volume: 500 $\mu$l) containing 20 mM substrate (various N-acetyl-D-amino acids) at 30° C. for 60 minutes. By measuring the amounts of amino acid synthesized by this reaction, enzymatic activities for respective substrates can be compared with each other. Assay for amino acid is performed by the TNBS (trinitrobenzenesulfonic acid) method or the HPLC method.

The enzyme activity is defined in units (U), assaying production of D-methionine as the standard, wherein 1 U is defined as the amount of enzyme that produces 1 $\mu$mol of D-methionine in 1 minutes at 30° C. Substrates other than D-methionine can be assayed by measuring the D-amino acid quantity produced in 1 minute at 30° C., as well. The reactivity between enzymes or substrates can be compared to each other utilizing this activity.

According to the results of the analysis discussed in detail below, the D-aminoacylase derived from the microorganisms belonging to the genus *Streptomyces* in the examples, were confirmed to catalyze especially well reactions of the following substrates (see Table 2):

N-acetyl-D-methionine;

N-acetyl-D-tryptophan; and

N-acetyl-D-phenylalanine.

Also catalytic actions on the following substrates were confirmed:

N-acetyl-D-valine;

N-acetyl-D-alanine; and

N-acetyl-D-leucine.

On the other hand, substantially no catalytic activity was confirmed on the following substrates:

N-acetyl-L-methionine;
N-acetyl-L-valine; and
N-acetyl-L-phenylalanine.

Thus, the present invention provides heat-stable D-aminoacylases that catalyze the reaction with N-acyl-D-amino acids to produce D-amino acids. The heat-stable D-aminoacylase is stable when treated under a pH of 7.5 at 55° C. for 60 minutes, and is inactivated at a temperature higher than 70° C. under the same condition. The term "stable" as used herein means that the activity is retained and includes comparative stability. Specifically, it can be referred to as being stable when at least 20%, preferably more than 40%, more preferably more than 60% of the activity, as compared to the activity before the treatment, is retained. On the other hand, "inactivated" refers to a situation where the activity drops markedly or a situation where the activity is totally lost. Specifically, in the case where is the activity drops to less than 10%, preferably less than 7%, and more preferably less than 5% of the activity compared to the activity before the treatment, it can be described as being inactivated. Activity can be measured as mentioned above.

Moreover, the heat-stable D-aminoacylase of the present invention shows optimal activity at a temperature around 60° C. when reacted at pH 7.5. The term "around 60° C." herein means a temperature of 55 to 65° C., preferably 57 to 63° C., and more preferably 58 to 62° C.

Further, the heat-stable D-aminoacylase of the present invention preferably shows a molecular weight of about 40,000 daltons measured by SDS-polyacrylamide gel electrophoresis. The term "about 40,000 daltons" encompasses a range of 35,000 to 45,000 daltons, preferably 37,000 to 43,000 daltons, and more preferably 38,000 to 42,000 daltons. Moreover, the heat-stable D-aminoacylase of the present invention preferably efficiently catalyzes the reaction with N-acetyl-D-methionine, N-acetyl-D-tryptophan and N-acetyl-D-phenylalanine, catalyzes the reaction with N-acetyl-D-valine, N-acetyl-D-alanine and N-acetyl-D-leucine, and has substantially no catalytic activity for N-acetyl-L-methionine, N-acetyl-L-valine and N-acetyl-L-phenylalanine. The term "efficiently catalyzes" as used herein means, substrates that are catalyzed at average or above the average. And the term "substantially no catalytic activity" means that no detectable L-amino acid is produced under the conditions above, or the activity calculated as above is less than 10, preferably less than 5, and more preferably less than 2 when taken the corresponding production activity of the D-amino acid to L-body is taken as 100.

Moreover, the heat-stable D-aminoacylase of the present invention shows optimal activity at a pH of about 7.0 when activated at 30° C. for 60 minutes. The term "a pH of about 7.0" encompasses a pH ranging from 6 to 8, preferably 6.3 to 7.7, and more preferably 6.5 to 7.5. Further, the activity is accelerated with 1 mM of $Co^{2+}$, and is inhibited markedly with 1 mM of $Cu^{2+}$. The acceleration of the activity should be a significant one. Furthermore, the term "marked inhibition of the activity" refers to a situation wherein the activity is decreased markedly or wherein the activity completely disappears. Specifically, it can be mentioned, "the activity is inhibited markedly" when the activity is decreased to under 10%, preferably under 5%, and more preferably under 3% compared to the activity where no 1 mM $Cu^{2+}$ exists. The activity can be measured and calculated as mentioned above.

There is no limitation on the derivation of the heat-stable D-aminoacylase of the present invention. Preferably the D-aminoacylase of the present invention is derived from microorganisms. For example, microorganisms that can proliferate under a condition with higher temperature than 55° C. like thermophile, thermophilic bacteria, and such can be mentioned as microorganisms for the preparation of the heat-stable D-aminoacylase of the present invention. Bacteria of the genus *Bacillus* (*B. thermophilus, B. megaterium, B. coagulans, B. stearothermophilus*, etc.), bacteria of the genus *Clostridium* (*C. kluyveri* and such), microorganisms of the genus *Desulfotomaculum* and such, as well as microorganisms of the genus *Thermus* (*T. flavus, T. thermophilus, T. aguaticus, T. celer*, etc.), methanogen (*Methanobacterium, Methanococcus, Methanosarcina*, etc.), lactic acid bacteria (*Lactobacillus lactis, L. acidophilus, L. bulgaricus, L. delbrueckii*, etc.), hydrogen bacteria, photosynthetic bacteria, and so on can be mentioned as thermophiles (thermophilic bacteria). Additionally, hyperthermophiles such as *Pyrococcus furisus, Pyrococcus sp.*, and *Aeropyrum pernix* and so on can be mentioned.

The heat-stable D-aminoacylase of the present invention is preferably a D-aminoacylase derived from a microorganism belonging to the genus *Streptomyces*. *Streptomyces thermonitrificans* is preferable as microorganisms belonging to the genus *Streptomyces*. For example, bacterial strain CS5-9 deposited as FERM BP-7678 can be mentioned as such a microorganism.

The D-aminoacylase produced by the microorganism can be obtained by culturing the microorganism, and recovering the culture or the culture supernatant. Either synthetic or natural media can be used, so long as they contain proper amounts of a carbon source, nitrogen source, inorganic materials, and other nutrients. The culture media may be either liquid or solid.

More specifically, examples of carbon sources include sugars such as glucose, fructose, maltose, galactose, starch, starch hydrolysate, molasses, and blackstrap molasses; natural carbohydrates such as wheat, barley, and corn; alcohols such as glycerol, methanol, and ethanol; fatty acids such as acetic acid, gluconic acid, pyruvic acid, and citric acid; hydrocarbons such as normal paraffin; and amino acids such as glycine, glutamine, and asparagine. One or more of the above carbon sources are used, depending on assimilability of the fungus used. Examples of nitrogen sources include organic nitrogen-containing compounds such as meat extract, peptone, yeast extract, soybean hydrolysate, milk casein, casamino acid, various amino acids, corn steep liquor, and other hydrolysates of animals, plants, and microorganisms; and inorganic nitrogen-containing compounds such as ammonia, ammonium salts such as ammonium nitrate, ammonium sulfate, ammonium chloride, nitrates such as sodium nitrate, and urea. One or more of the above nitrogen sources are used, depending on assimilability of the fungus.

Furthermore, a minute amount of one or more inorganic salts can be used. Examples thereof include phosphates; hydrochlorides; nitrates; acetates; or similar salts of magnesium, manganese, potassium, calcium, sodium, copper, or zinc. Antifoaming agents, such as vegetable oil, surfactants, or silicon, may be added to the culture medium.

Culturing can be performed in the liquid medium containing the above-described ingredients using the usual culture methods, such as shaking culturing, aerobic agitation culturing, continuous culturing, or fed-batch culturing.

Culturing conditions may be properly selected depending upon the fungal strain and culture method, and are not particularly limited as long as the fungi used can proliferate to produce D-aminoacylase. Ordinarily, the pH at the beginning of the cultivation is adjusted to pH 4 to 10, preferably to 6 to 8. A temperature that suits for the growth of the microorganism is selected conveniently.

The culturing time is also not particularly limited so long as a sufficient amount of fungal cells having the D-aminoacylase activity can be obtained. The culturing is usually performed for 1 to 14 days, preferably for 1 to 3 days. The D-Aminoacylase produced and accumulated with gene expression can be recovered and isolated by the following methods.

When D-aminoacylase is intracellularly produced, the fungal cells are collected by the method such as filtration or centrifugation after the culturing and washed with buffer, physiological saline, etc. The enzyme can then be extracted by disrupting the fungal cells using physical means, such as freeze-thawing, ultrasonication, compression, osmotic treatment, or trituration; using biochemical means, such as cell wall lysis with lysozyme; or using chemical means, such as surfactant treatment. One or more of these treatments can be combined. The crude D-aminoacylase thus obtained can be purified by a single or combined fractionation means, including salting out; fractional precipitation with organic solvents, etc.; various chromatographies, such as salting-out chromatography, ion-exchange chromatography, gel filtration chromatography, hydrophobic chromatography, dye chromatography, hydroxylapatite chromatography, or affinity chromatography; and electrophoresis, such as isoelectric focusing and native electrophoresis. The above chromatographies can be performed using open columns or by means of medium-pressure or high-performance liquid chromatography (HPLC).

Specifically, the D-aminoacylase can be prepared for example by the purification method described in the example below. That is, cultivation with shaking is conducted in a medium for example, like 231 liquid culture medium (0.1% yeast extract, 0.1% meat extract, 1.0% maltose, 0.2% N.Z.amine type A, pH 7.0), and harvested by centrifugation. The obtained cell body is fragmented by ultrasonication with a sonicator, and the crude enzyme solution of the D-aminoacylase is obtained by recovering the supernatant by centrifugation. Thereafter, precipitation treatment using ammonium sulfate, desalting by gel filtration, Butyl-Toyopearl 650M hydrophobic chromatography, DEAE-Toyopearl 650M ion-exchange chromatography, Sephacryl S200 gel filtration chromatography, MonoQ ion exchange chromatography is conducted to purify the enzyme as a single band by SDS-polyacrylamide gel electrophoresis.

By utilizing the D-aminoacylase of the present invention, it is possible to isolate the DNA encoding the same. The DNA encoding the D-aminoacylase of the present invention can be isolated, for example, by the following method.

After purification of the enzyme of the present invention, the N-terminal amino acid sequence is analyzed. Then, it is digested with enzymes such as lysylendopeptidase and V8 protease, and the peptide fractions are purified by reverse phase liquid chromatography. Thereafter, many amino acid sequences can be determined by analyzing amino acid sequence by protein sequencer.

PCR primers are designed based on the determined amino acid sequence, and a part of the DNA encoding the D-aminoacylase of the present invention can be obtained by conducting PCR, using the genomic DNA or cDNA library of the enzyme-producing strain as the template, and a PCR primer designed based on the amino acid sequence.

Moreover, DNA encoding the D-aminoacylase of the present invention can be obtained by using the obtained DNA fragment as the probe, by inserting the restriction enzyme digest of the genomic DNA of the enzyme-producing strain into a phage or plasmid and such, transforming the E. coli with it to obtain the library or cDNA library, and conducting colony hybridization, plaque hybridization, and so on.

It is also possible to obtain the DNA encoding the D-aminoacylase of the present invention by first analyzing the base sequence of the obtained DNA fragment by PCR, and thereafter, designing a PCR primer to elongate the known DNA outside. After digesting the genomic DNA of the enzyme-producing strain with an appropriate restriction enzyme, reverse PCR is performed using the DNA as the template, by the self cyclization reaction (Genetics 120, 621–623 (1988)), the RACE method (Rapid Amplification of cDNA End, "PCR experimental manual" p25–33 HBJ press) and such. The DNA encoding a D-aminoacylase of the present invention include not only the genomic DNA and cDNA cloned by the above-mentioned methods but also chemically synthesized DNA.

The isolated DNA encoding the D-aminoacylase of the present invention is inserted into a known expression vector to provide a D-aminoacylase-expressing vector. Further, by culturing cells transformed with the expression vector, the D-aminoacylase of the present invention can be obtained from the transformed cells.

There is no restriction on the microorganism to be transformed for D-aminoacylase expression in the present invention, so long as the organism is capable of being transformed with the vector containing the recombinant DNA encoding the this D-aminoacylase and capable of expressing D-aminoacylase activity. Available microorganisms are those for which host-vector systems are available and include, for example:

bacteria such as the genus *Escherichia*, the genus *Bacillus*, the genus *Pseudomonas*, the genus *Serratia*, the genus *Brevibacterium*, the genus *Corynebacterium*, the genus *Streptococcus*, and the genus *Lactobacillus*;

actinomycetes such as the genus *Rhodococcus* and the genus *Streptomyces*;

yeasts such as the genus *Saccharomyces*, the genus *Kluyveromyces*, the genus *Schizosaccharomyces*, the genus *Zygosaccharomyces*, the genus *Yarrowia*, the genus *Trichosporon*, the genus *Rhodosporidium*, the genus *Hansenula*, the genus *Pichia*, and the genus *Candida*; and fungi such as the genus *Neurospora*, the genus *Aspergillus*, the genus *Cephalosporium*, and the genus *Trichoderma*; etc.

Procedure for the preparation of a transformant and construction of a recombinant vector suitable for a host can be carried out by employing techniques that are commonly used in the fields of molecular biology, bioengineering, and genetic engineering (for example, see Sambrook et al., "Molecular Cloning", Cold Spring Harbor Laboratories). In order to express the DNA encoding the D-aminoacylase of the present invention in a microorganism, it is necessary to introduce the DNA into a plasmid vector or phage vector that is stable in the microorganism and allow the genetic information transcribed and translated. To do so, a promoter, a unit for regulating transcription and translation, is typically placed upstream of the 5' end of the DNA encoding D-aminoacylase, and preferably a terminator is placed downstream of the 3' end of the DNA. The promoter and the terminator should be functional in the microorganism to be utilized as a host. Available vectors, promoters, and terminators for the above-mentioned various microorganisms are described in detail in "Fundamental Course in Microbiology (8): Genetic Engineering", Kyoritsu Shuppan, specifically for yeasts, in "Adv. Biochem. Eng. 43, 75–102(1990)" and "Yeast 8, 423–488 (1992)."

For example, for the genus *Escherichia*, in particular, for *Escherichia coli*, available plasmids include the pBR series and pUC series plasmids; available promoters include promoters derived from lac (derived from β-galactosidase gene), trp (derived from the tryptophan operon), tac and trc (which are chimeras of lac and trp), $P_L$ and $P_R$ of λ phage, etc. Available terminators are derived from trpA, phages, rrnB ribosomal RNA, etc.

For the genus *Bacillus*, available vectors are the pUB110 series and pC194 series plasmids; the vectors can be integrated into host chromosome. Available promoters and terminators are derived from apr (alkaline protease), npr (neutral protease), amy (α-amylase), etc.

For the genus *Pseudomonas*, there are host-vector systems developed for *Pseudomonas putida* and *Pseudomonas cepacia*. A broad-host-range vector, pKT240, (containing RSF1010-derived genes required for autonomous replication) based on TOL plasmid, which is involved in decomposition of toluene compounds, is available; a promoter and a terminator derived from the lipase gene (Unexamined Published Japanese Patent Application (JP-A) No. Hei 5-284973) are available.

For the genus *Brevibacterium*, in particular, for *Brevibacterium lactofermentum*, available plasmid vectors include pAJ43 (Gene 39, 281 (1985)). Promoters and terminators used for *Escherichia coli* can be utilized without any modification for *Brevibacterium*.

For the genus *Corynebacterium*, in particular, for *Corynebacterium glutamicum*, plasmid vectors such as pCS11 (JP-A No. Sho 57-183799) and pCB101 (Mol. Gen. Genet. 196, 175(1984)) are available.

For the genus *Streptococcus*, plasmid vectors such as pHV1301 (FEMS Microbiol. Lett. 26, 239 (1985)) and pGK1 (Appl. Environ. Microbiol. 50, 94 (1985)) can be used.

For the genus *Lactobacillus*, plasmid vectors such as pAMβ1 (J. Bacteriol. 137, 614 (1979)), which was developed for the genus *Streptococcus*, can be utilized; and promoters that are used for *Escherichia coli* are also usable.

For the genus *Rhodococcus*, plasmid vectors isolated from *Rhodococcus rhodochrous* are available (J. Gen. Microbiol. 138, 1003 (1992)).

For the genus *Streptomyces*, plasmids can be constructed in accordance with the method as described in "Genetic Manipulation of *Streptomyces*: A Laboratory Manual" (Cold Spring Harbor Laboratories (1985)) by Hopwood et al. In particular, for *Streptomyces lividans*, pIJ486 (Mol. Gen. Genet. 203, 468–478, 1986), pKC1064 (Gene 103, 97–99 (1991)), and pUWL-KS (Gene 165, 149–150 (1995)) are usable. The same plasmids can also be utilized for *Streptomyces virginiae* (Actinomycetol. 11, 46–53 (1997)).

For the genus *Saccharomyces*, in particular, for *Saccharomyces cerevisiae*, the YEp series, YEp series, YCp series, and YIp series plasmids are available; integration vectors (refer EP 537456, etc.), which are integrated into chromosome via homologous recombination with multicopy-ribosomal genes, allow to introduce a gene of interest in multicopy and the gene incorporated is stably maintained in the microorganism; and thus, these types of vectors are highly useful. Available promoters and terminators are derived from genes encoding ADH (alcohol dehydrogenase), GAPDH (glyceraldehyde-3-phosphate dehydrogenase), PHO (acid phosphatase), GAL (β-galactosidase), PGK (phosphoglycerate kinase), ENO (enolase), etc.

For the genus *Kluyveromyces*, in particular, for *Kluyveromyces lactis*, available plasmids are those such as 2-μm plasmids derived from *Saccharomyces cerevisiae*, pKD1 series plasmids (J. Bacteriol. 145, 382–390(1981)), plasmids derived from pGK11 and involved in the killer activity, KARS (Kluyveromyces autonomous replication sequence) plasmids, and plasmids (refer EP 537456, etc.) capable of being integrated into chromosome via homologous recombination with the ribosomal DNA. Promoters and terminators derived from ADH, PGK, and the like are available.

For the genus *Schizosaccharomyces*, it is possible to use plasmid vectors comprising the ARS (autonomous replication sequence) derived from *Schizosaccharomyces pombe* and auxotrophy-complementing selectable markers derived from *Saccharomyces cerevisiae* (Mol. Cell. Biol. 6, 80 (1986)). Promoters such as ADH promoter derived from *Schizosaccharomyces pombe* are usable (EMBO J. 6, 729 (1987)). In particular, pAUR224 is commercially available from TaKaRa Shuzo Co., Ltd.

For the genus *Zygosaccharomyces*, plasmids originating from those such as pSB3 (Nucleic Acids Res. 13, 4267 (1985)) derived from *Zygosaccharomyces rouxii* are available; it is possible to use promoters such as the PHO5 promoter derived from *Saccharomyces cerevisiae* and GAP-Zr (Glyceraldehyde-3-phosphate dehydrogenase) promoter (Agri. Biol. Chem. 54, 2521 (1990)) derived from *Zygosaccharomyces rouxii*.

For the genus *Hansenula*, host-vector systems have been developed for *Hansenula polymorpha*. *Hansenula polymorpha*-derived autonomous replication sequences, HARS1 and HARS2, may be utilized as vectors, but the replication sequences are relatively unstable, and accordingly multicopy integration into chromosome is an effective way to ensure stable introduction of genes (Yeast 7, 431–443 (1991)). Promoters such as that of the AOX (alcohol oxidase) gene, of which expression is induced by methanol or the like, and a promoter from the FDH (formic acid dehydrogenase) are available.

For the genus *Pichia*, host-vector systems originating from autonomous replication sequences (PARS1, PARS2) derived from *Pichia* have been developed (Mol. Cell. Biol. 5, 3376 (1985)), and it is possible to employ a highly efficient promoter, such as the methanol-inducible AOX promoter, which is available for high-cell-density-culture (Nucleic Acids Res. 15, 3859 (1987)).

For the genus *Candida*, host-vector systems have been developed for *Candida maltosa, Candida albicans, Candida tropicalis, Candida utilis*, etc. An autonomous replication sequence originating from *Candida maltosa* has been cloned (Agri. Biol. Chem. 51, 51, 1587 (1987)), and a vector using the sequence has been developed for *Candida maltosa*.

Further, a chromosome-integration vector with a highly efficient promoter unit has been developed for *Candida utilis* (JP-A No. Hei 08-173170).

For the genus *Aspergillus, Aspergillus niger* and *Aspergillus oryzae* have intensively been studied among fungi, and thus plasmid vectors and chromosome-integration vectors are available, as well as promoters derived from an extracellular protease gene and amylase gene (Trends in Biotechnology 7, 283–287 (1989)).

For the genus *Trichoderma*, host-vector systems have been developed for *Trichoderma reesei*, and promoters such as that derived from an extracellular cellulase gene are available (Biotechnology 7, 596–603 (1989)).

There are various host-vector systems developed for plants and animals other than microorganisms; in particular, the systems include those of insect such as silkworm (Nature 315, 592–594 (1985)), and plants such as rapeseed, maize, potato, etc.

Various kinds of strains having D-aminoacylase production ability are encompassed by the present invention including mutant strains, mutation, and transformed strains with acquired production ability of the D-aminoacylase of the present invention made by the utilization of the gene manipulation technique.

A foreign gene contained in the transformant is induced under appropriate conditions given in a growth phase or after full growth. For example, in the case of lac promoter, addition of IPTG induces the expression of the foreign gene that is connected downstream of the promoter. As for a temperature-sensitive promoter, the culture is performed at a temperature required for the expression.

Cultivation of the D-aminoacylase-producing strain (including organisms transformed by the D-aminoacylase expression vector), and purification of the D-aminoacylase can be done by the same method as above. The obtained D-aminoacylase can be utilized in the production of D-amino acids. Moreover. The culture can be used in the D-amino acid production as it is, or as a crude purification product by fracturing the cell body. That is, the cell body cultured on the liquid medium or the plate medium is harvested, and the immobilized cell body, crude enzyme, immobilized enzyme and so on is prepared as occasion demands. The D-amino acid production reaction system is constructed by contacting it with the material, N-acyl-DL-amino acid. The N-acyl-DL-amino acid may be resolved in an appropriate solvent. The reaction can be carried out in an aqueous media with a buffering ability such as phosphate buffer, a mixed media of aqueous media to which 1 to 100% water-soluble organic solvent like methanol, ethanol, acetone and so on is mixed, and a two phase system of a aqueous media and non-water soluble solvent which fails to dissolve in water, such as, n-hexane, ethyl acetate, isopropyl acetate, n-butyl acetate, hexane, toluene, chloroform, and so on. In a two-phase system, the D-aminoacylase, as well as the cell body and the reactant cell body is provided as it is, or as solutions in water or buffers. Alternatively, the N-acyl-DL-amino acid can be provided to the reaction system resolved in an aqueous solvent such as water, buffer, ethanol, and so on. In this case, the D-aminoacylase, as well as the cell body or the reactant cell body constitutes a reaction system with a singular phase. Alternatively, the reaction of the present invention can be carried out utilizing immobilized enzymes, membrane reactors and such. However, the configuration of the contact of the enzyme with the reaction solution is not limited to these specific examples. A reaction solution is a convenient solvent, which provides a desirable environment for expression of the enzyme activity, to which the substrate is dissolved.

The heat-stable D-aminoacylase of the present invention has a property to produce D-amino acid, catalyzing reactions with various N-acyl-D-amino acids under higher temperature regions as compared to those of formerly known enzymes. Therefore, the solubility of the material and substrate elevates. And the concentration of the preparation can be set higher. Therefore, using the heat-stable D-aminoacylase of the present invention it is possible to produce the D-amino acid in a much industrially efficient way. For example, D-amino acid can be selectively produced by reacting D-aminoacylase of this invention with N-acyl-DL-amino acid, a mixture of D- and L-enantiomers.

N-acyl-DL-amino acids used in the present invention are not particularly limited and can be selected from a wide variety of compounds. A typical N-acyl-DL-amino acid can be represented by the formula (I):

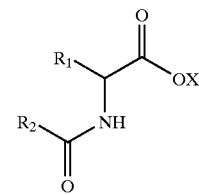

[Formula 1]

where $R_1$ and $R_2$ may be identical or different and each represents a hydrogen atom or a substituted or unsubstituted hydrocarbon group; preferably, the hydrocarbon group represented by $R_1$ and $R_2$ is alkyl, alkenyl, alkynyl, cycloalkyl, aryl, or aralkyl, or the derivative thereof, and may be further substituted, provided that $R_2$ does not represent a hydrogen atom; and X is H, $NH_4$, or a metal ion.

The derivative used herein means those of alkyl, alkenyl, alkynyl, cycloalkyl, aryl, or aralkyl substituted with alkyl, alkenyl, alkynyl, cycloalkyl, aryl, aralkyl, hydroxy, halogen, amino, thio, methylthio, or the like; or aryl or aralkyl of which aromatic ring moiety is a heterocycle comprising one or more nitrogen(s) or sulfur(s).

Specific examples of the hydrocarbon group contain from 1 to 10 carbon atoms, including linear or branched alkyl having 1 to 6 carbon atoms, such as methyl, ethyl, n-propyl, i-propyl, n-butyl, i-butyl, sec-butyl, t-butyl, n-pentyl, i-pentyl, n-hexyl, etc.; alkenyl having 1 to 6 carbon atoms such as ethenyl, 1-propenyl, 2-propenyl, 1-butenyl, 2-butenyl, 2-pentenyl, 4-pentenyl, 1-hexenyl, 3-hexenyl, 5-hexenyl, etc.; alkynyl having 1 to 6 carbon atoms such as ethynyl, 1-propynyl, 2-pentynyl, etc.; aryl such as phenyl, naphthyl, etc.; cycloalkyl such as cyclopropyl, cyclobutyl, cyclopentyl, cyclohexyl, etc. The substituent of the hydrocarbon group for R1 and R2 includes halogen; alkyl as defined above; alkenyl as defined above; alkynyl as defined above; aryl as defined above; heterocyclic such as piridyl, indole, quinolyl, etc.; amino; hydroxyl; thio; etc. The metal ion represented by X includes sodium, patassium, etc.

Methyl, chloromethyl, phenyl, and aminomethyl, which may be substituted with the above substituent(s), can be mentioned as preferable $R_2$. Thiomethylethyl (for N-acyl-DL-methionine), isopropyl (for N-acyl-DL-valine), 3-indolylmethyl (for N-acyl-DL-tryptophan), carbamoylmethyl (for N-acyl-DL-asparagine), benzyl (for N-acyl-DL-phenylalanine), methyl (for N-acyl-DL-alanine), and 2-methylpropyl (for N-acyl-DL-leucine) can be mentioned as preferable $R_1$.

N-acetyl-DL-amino acid is especially preferable as the substrate, to which the heat-stable D-aminoacylase of the present invention is acted, and for example, N-acetyl-DL-methionine, N-acetyl-DL-valine, N-acetyl-DL-tryptophan, N-acetyl-DL-asparagine, N-acetyl-DL-phenylalanine, N-acetyl-DL-alanine, and N-acetyl-DL-leucine can be preferably exemplified.

D-Aminoacylase used for producing D-amino acid in the present invention includes the partially purified enzyme as well as the purified one. Moreover, the present invention includes D-aminoacylase stabilized on insoluble carrier by well-known method. Besides these enzyme proteins, the D-aminoacylase-producing microbe can also be used in the present invention. Namely, D-amino acid can be produced by directly reacting the microbe capable of producing D-aminoacylase with N-acetyl-DL-amino acid. Further, it is possible to produce D-amino acids by reacting N-acetyl-DL-amino acids to the reactant microorganisms. The term "reactant microorganisms" includes those treated by physical treatment, such as freezing and thawing methods, ultrasonication, pressure, osmotic pressure difference, and grinding; biochemical treatment, such as treatment by cell wall lysing enzymes like lysozyme; or by chemical treatment, such as treatment by contacting to organic solvents like detergents, toluene, xylene, acetone, and so on. Microorganisms with changed permeability of the cell membrane by such treatment, or cell-free extracts in which cell bodies are disintegrated by treatment with glass beads or enzymes, or those partly purified are included in "reactant microorganisms".

D-aminoacylase or microbes capable of producing the enzyme or its treatment of present invention is reacted with N-acyl-D-amino acid under conditions suitable for the activity and stability of D-aminoacylase, and for the reactivity of the transformant. Some D-aminoacylases are activated or inhibited by divalent metal ions, such as $Zn^{2+}$, $Ni^{2+}$, $Co^{2+}$ and $Cu^{2+}$. When enzyme activity is inhibited by a divalent metal ion, a chelating reagent such as EDTA can be added.

Though the concentration of the substrate, N-acetyl-DL-amino acid, is not particularly limited, it is usually employed at a concentration of about 0.1 to 50 w/v %.

The substrate does not have to be completely dissolved in the reaction medium. Additionally, the substrate can be added at the beginning of the reaction, but it is convenient to add it continuously or intermittently so that the substrate concentration in the reaction liquid does not rise too high. The reaction may proceed earlier in most cases, where large quantities of D-aminoacylases are used; however, an amount of 1 U to 1000 U/ml of the enzyme is normally used. The reaction temperature may be set up according to the thermal stability of the enzyme, but is usually in the range of 5 to 70° C. Further, the reaction pH may be any amount where the enzyme acts, but is usually a pH 4 to 10. The reaction may be conducted with stirring or without stirring.

In general, an enzyme or a microorganism can be stabilized by immobilization. Immobilization can be done by any known method, on a suitable carrier such as polyacrylamide gel, sulfur-containing polysaccharide gel (carrageenan gel), alginic acid gel, chitin, cellulose or agar gel. Moreover, previous methods utilize cross-linking-treated carriers, such as glutaraldehyde. The time required for the reaction with the immobilized enzyme or microorganism depends on the amounts of both D-aminoacylase and substrate. One skilled in the art can empirically optimize these conditions as the most ideal ones. Usually, ten- to one hundred-hour reaction efficiently produces a desired reaction product.

The D-amino acids produced can be recovered by a known method such as direct crystallization by concentration or isoelectric precipitation, ion exchange resin treatment, membrane filtration, or the like. For example, D-tryptophan produced using N-acetyl-DL-tryptophan as a substrate can be purified as follows. After the enzymatic reaction, the reaction mixture is contacted with a strongly acidic cation exchange resin to adsorb D-tryptophan. The resin is washed with water and D-tryptophan is eluted with 0.5 N aqueous ammonia. After the eluate is concentrated, the thus-obtained crude crystalline powder of D-tryptophan is dissolved in a small amount of 50% hot ethanol, decolorized with activated charcoal, and cooled to obtain purified crystals of D-tryptophan.

In the method of the present invention, D-valine can be purified as follows. After the enzymatic reaction, the microbial cells are removed by centrifugation or the like, and the resulting supernatant is adjusted to pH 1 by adding 6 N hydrochloric acid. The precipitated N-acetyl-L-valine is removed by centrifugation. The supernatant is treated with activated charcoal, adjusted to pH 7.0, then added to an $H^+$-type strongly acidic cation exchanger (Amberlite IR-120B). Elution is performed with 5% aqueous ammonia, and the resulting eluate is dried at 80° C. under reduced pressure, thereby obtaining purified D-valine.

According to the present invention, a heat-stable D-aminoacylase derived from *Streptomyces thermonitrificans*, as well as preparation method for D-amino acid using the same is provided. By utilizing the heat-stable D-aminoacylase, it is possible to produce readily and efficiently the corresponding D-amino acids from N-acetyl-DL-amino acids (for example, N-acetyl-DL-methionine, N-acetyl-DL-valine, N-acetyl-DL-tryptophan, N-acetyl-DL-phenylalanine, N-acetyl-DL-alanine, N-acetyl-DL-leucine, and so on).

Any patents, patent applications, and publications cited herein are incorporated by reference.

The present invention is described in more detail with reference to the following examples but is not to be construed to be limited thereto.

EXAMPLE 1

(1) Identification of the Strain

The properties of CS5-9, isolated from the soil of Shizuoka prefecture, was as follows. The color of the aerial hypha was gray and that of the substrate hypha had no color, and no diffusion melanin pigment was seen. The linkage form of the spore was spiral, and the sporophore was generally straight but was rarely observed to be spiral in an ISP medium containing glucose. It can utilize D-glucose, D-fructose, sucrose, and inositol, but it cannot grow on L-arabinose, D-xylose, D-mannitol, raffinose, or rhamnose. The LL-diaminopimelic acid is the main fatty acid composition of the cell wall. The identity analysis of the 16S rRNA base sequence by direct sequencing with PCR revealed 100% identity with *Streptomyces themonitrificans* DSM 40579 (ISP 5579). Thus, the CS5-9 strain was identified as belonging to the *Streptomyces thermonitrificans* based on the ISP (International Streptomyces Project) and Bergey's manual of Systematic Bacteriology (Volume 4) 1989.

This strain was deposited as "*Streptomyces thermonitrificans* CS5-9" with the following depositary institution.

(i) Name and address of the depositary institution.
  name: National Institute of Bioscience and Human-Technology, Agency of Industrial Science and Technology, Ministry of International Trade and Industry
  address: (zip code 305-0046)
    1-1-3, Higashi, Tsukuba-shi, Ibaraki 305, Japan
(ii) Date of deposit (first day when it was deposited)
  Jul. 11, 2000
(iii) Accession No. FERM BP-7678

(2) Strain and Cultivation

The culture media to produce D-aminoacylase with *Streptomyces thermonitrificans* CS5-9 was prepared by pouring 120 ml of 231 liquid media (0.1% yeast extract (Oriental Yeast, Co., ltd.), 0.1% meat extract, 1.0% maltose, 0.2% N.Z.amine type A, pH 7.0) to each 500-ml volume Sakaguchi flask, and sterilized in an autoclave (Speedclave, Kurihara medical instruments). The culture was conducted on a shaker at 115 spm. for 42 hours at 50° C. 5 ml liquid media with the same composition was poured into a test tube and was sterilized in a Speedclave to seed a volume of platinum loop from the slant (TBS agar media (0.4% polypeptone, 0.05% glucose, 0.5% NaCl, 0.25% $K_2HPO_4$, 2% agar, pH 7.3)) and to culture with shaking at 50° C. for 24 hours as a preculture.

After cultivation, centrifugation (Hitachi Koki, himac SCR20B, RPR10-2 rotor) at 8,000 rpm (12,500×g) for 10 minutes at 4° C. was conducted to harvest the fungus. After washing the harvested fungus with 50 mM phosphate buffer (pH 7.0), it was centrifuged in the same rotor at 4,000 rpm (3,130×g) for 10 minutes at 4° C. to obtain the fungus to be used. The obtained fungus was kept at −20° C.

(3) Method for D-aminoacylase Activity Measurement

The fungus obtained as above was disintegrated in 50 mM phosphate buffer (pH 7.0) by ultrasonication with a sonicator (Kubota, Insonator 201M) at 190 W for 15 minutes. Then, it was subjected to centrifugation by a cooling centrifuge (Hitachi Koki) using an RPM20-2 rotor at 17,500 rpm (39,000×g) for 15 minutes at 4° C. to obtain the supernatant. This was used as the crude enzyme solution of D-aminoacylase.

The measurement of the enzyme activity was proceeded according to the TNBS method (Tokuyama, S., Hatano, K., and Takahashi, T., Biosci.Biotech.Biochem. 58:24(1994)). That is, the sample containing the amino acid was added to 0.5 ml of solution (C) (0.1 M $Na_2B_4O_7$) to give a total volume of 1.0 ml. 20 ml of 0.11 M TNBS solution was added with stirring immediately. The absorbance at 420 nm was measured after 5 minutes.

D-methionine was measured colorimetrically using L-methionine as a standard, and the amount of enzyme-producing 1 μmol of D-methionine in 1 minute at 30° C. was determined 1 unit.

The assay of the protein was conducted according to the method of Lowry using BSA (Bovine Serum Albumin, Sigma) as the standard. That is, before measurement, an alkaline copper solution, which is a 50:1 mixture of solution (A) (2% $Na_2CO_3$ (in 0.1 N NaOH)) and solution (B) (0.5% $CuSO_4$ $5H_2O$ (in 1% sodium citrate), was prepared and 1 ml of the alkaline copper solution was added to the protein sample (5 to 50 μg of proteins). Allowing it to stand still for 20 minutes at room temperature, 0.1 ml of phenol reagent (acid concentration 1 N) diluted with 2 volumes of distilled water was added and was left for 30 minutes at room temperature. Then, the absorbance at 750 nm was measured.

EXAMPLE 2

Purification of the heat-stable D-aminoacylase derived from *Streptomyces thermonitrificans*.

(1) Cultivation of the Fungus

The culture media for the production of D-aminoacylase by *Streptomyces thermonitrificans* CS5-9 strain was prepared by pouring 120 ml of 231 liquid media (0.1% yeast extract (Oriental Yeast, Co., ltd.), 0.1% meat extract, 1.0% maltose, 0.2% N.Z.amine type A, pH 7.0) to each 500 ml volume Sakaguchi flask, and sterilizing in a Speedclave (Kurihara medical instruments). The culture was conducted on a shaker at 115 spm. for 42 hours at 50° C. 5 ml liquid media with the same composition was poured into a test tube and was sterilized in a Speedclave to seed a volume of platinum loop from the slant (TBS agar media (0.4% polypeptone, 0.05% glucose, 0.5% NaCl, 0.25% $K_2HPO_4$, 2% agar, pH 7.3)) and to culture with shaking at 50° C. for 24 hours as a preculture.

After cultivation, centrifugation (Hitachi Koki, himac SCR20B, RPR10-2 rotor) at 8,000 rpm (12,500×g) for 10 minutes at 4° C. was conducted to harvest the fungus. After washing the harvested fungus with 50 mM phosphate buffer (pH 7.0), it was centrifuged in the same rotor at 4,000 rpm (3,130×g) for 10 minutes at 4° C. to obtain the fungus to be used. The obtained fungus was kept at −20° C.

(2) Purification of D-aminoacylase

Purification procedure was carried out at 4° C. except otherwise stated. 50 mM phosphate buffer (pH 7.0) was used as the buffer.

(2-1) Preparation of the Crude Enzyme Solution 980 g of wet fungus were suspended in 3 volumes of 50 mM phosphate buffer (pH 7.0), and were ultrasonicated at 190 W for 25 minutes. Then it was centrifuged (himac SCR20B HITACHI RPR10-2 rotor, 8,000 rpm (12,500×g), 15 min, 4° C.) to give a crude enzyme solution (2.35 L).

(2-2) Butyl-Toyopearl 650M Column Chromatography

Figure 1:
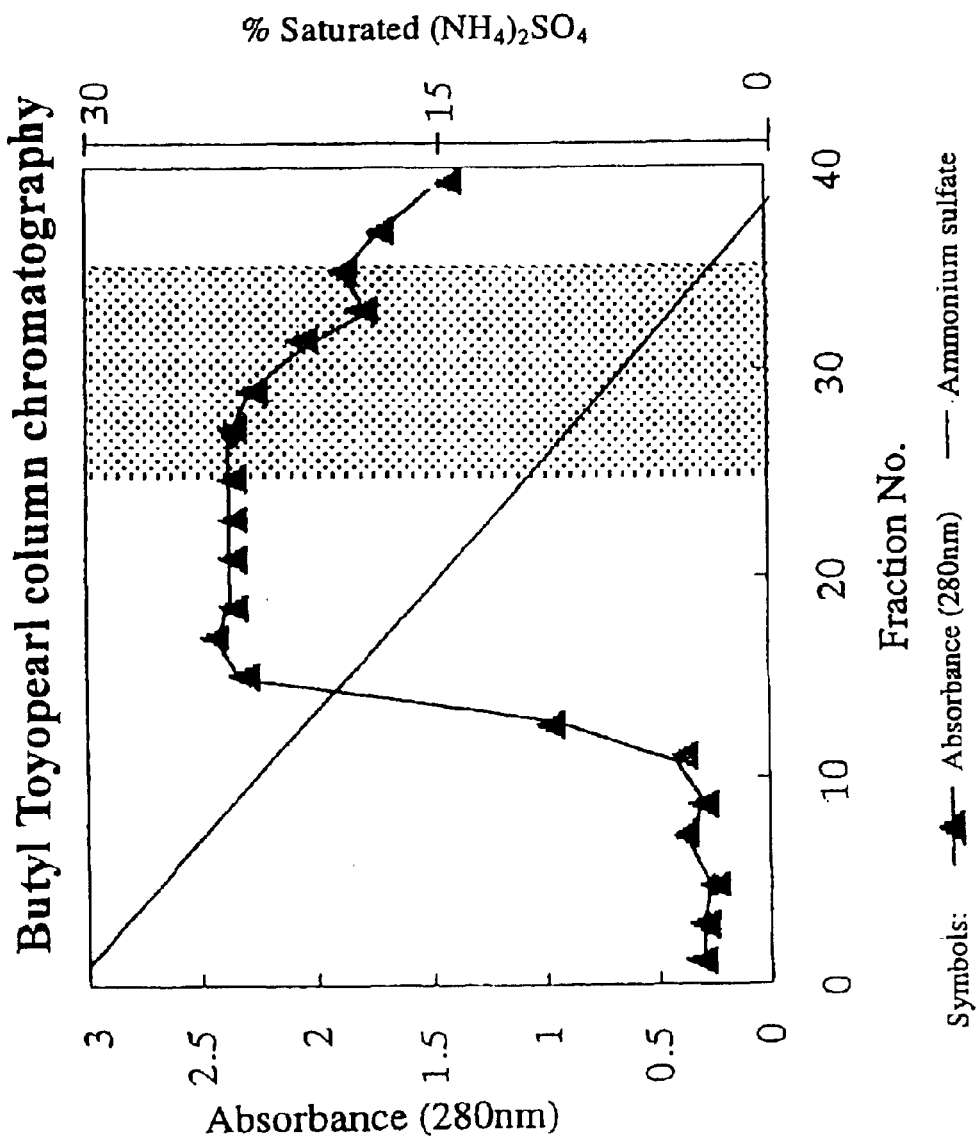
FIG. 1 illustrates purification by Butyl-Toyopearl column chromatography of the D-aminoacylase of the present invention. The triangle denotes the absorbance (at 280 nm); the line denotes the concentration of ammonium sulfate (by % saturation). The active fraction is denoted by arrows (fraction numbers from 25 to 35). Additional parameters include:
   gel volume: 180 ml;
   resin: TK Butyl Toyopearl 650M;
   equilibration and washing: 30% saturated ammonium sulfate containing 50 mM phosphate buffer 800 ml; and
   elution: 800 ml of buffer with a linear gradient of 30% to 0% saturated ammonium sulfate, each fraction contained 20 ml solution.
Figure 2:
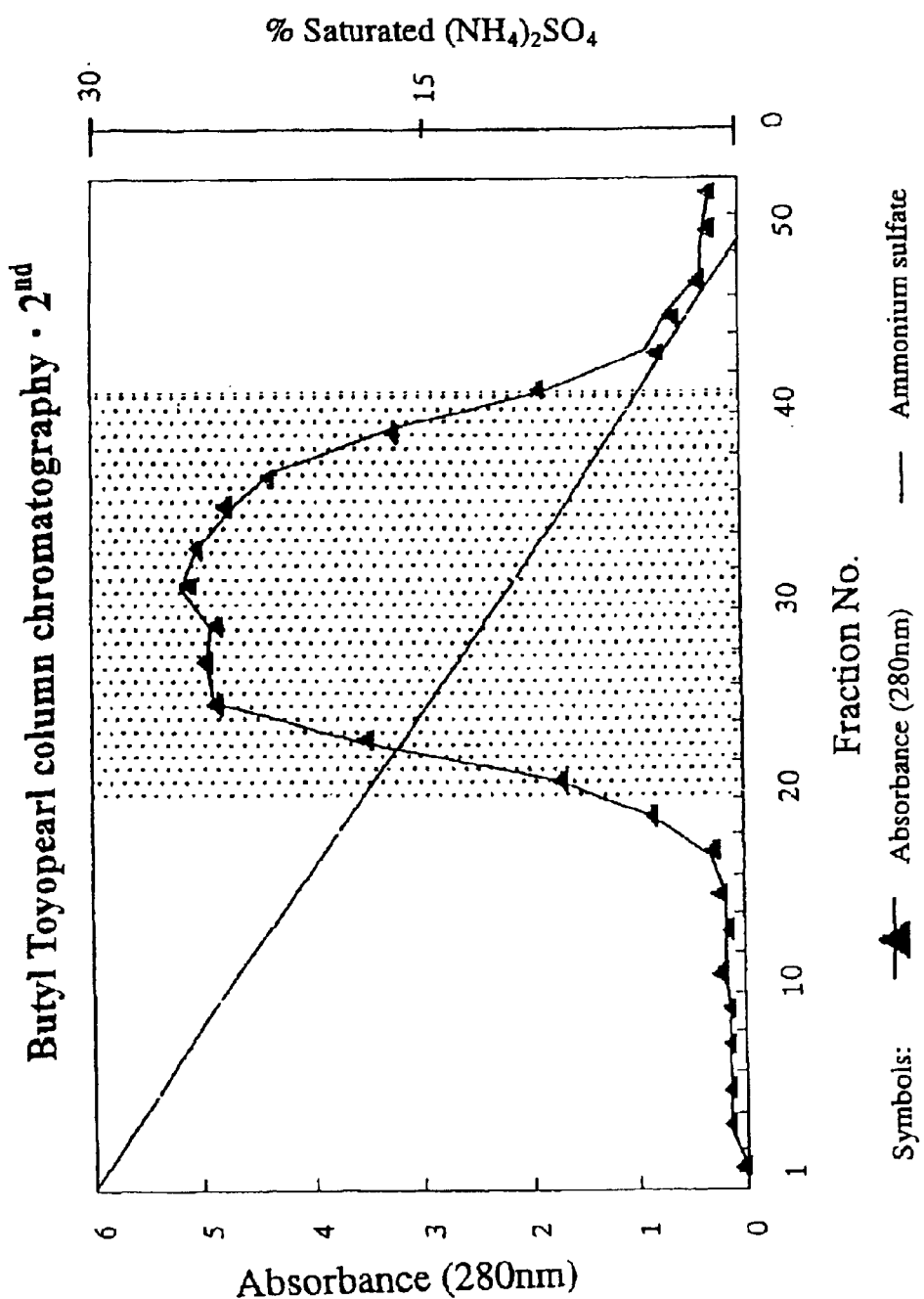
FIG. 2 illustrates purification by Butyl-Toyopearl column chromatography (2 nd) of the D-aminoacylase of the present invention. The triangle denotes the absorbance (at 280 nm); the line denotes the concentration of ammonium sulfate (by % saturation). The active fraction is denoted by arrows (fraction numbers from 20 to 415). Additional parameters include:
   gel volume: 50 ml
   resin: TK Butyl Toyopearl 650M
   equilibration and washing: 30% saturated ammonium sulfate containing 50 mM phosphate buffer 800 ml
   elution: 800 ml of buffer with a linear gradient of 30% to 0% saturated ammonium sulfate, each fraction contained 20 ml solution.

To give a 30% saturated solution, ammonium sulfate was added to the crude enzyme solution. The mixture was allowed to stand still for 1 hour at 0° C., then it was centrifuged (17,500 rpm ×30 minutes). The supernatant was absorbed on a Butyl-Toyopearl 650M column (200 ml), previously equilibrated with a buffer containing 30% saturated ammonium sulfate. The column was washed with 1000 ml of the same buffer. Then was eluted with 1000 ml of the buffer decreasing the concentration of ammonium sulfate from 30% saturated to 0% to obtain the active fraction (100 ml). Ammonium sulfate was added to the active fraction to 60% saturation, and the mixture was allowed to stand still for 1 hour at 0° C., and was centrifuged (17,500 rpm ×30 minutes). After the precipitate was rinsed with the buffer, it was diluted in the buffer (30 ml). By conducting Butyl-Toyopearl 650M column chromatography, the enzyme of the present invention absorbed at a concentration of 30% saturated ammonium sulfate, and no activity of the enzyme of the present invention was observed in the wash through fraction and washing fraction, but was in the elution fraction (FIG. 1).

(2-3) Desalting Gel Filtration by Sephadex G-25

The above concentrated solution (30 ml) was gel filtrated to desalt with SephadexG-25 (100 ml), equilibrated in advance with 300 ml of buffer containing 50 mM NaCl.

(2-4) Butyl-Toyopearl 650M Column Chromatography

To reach 30% saturation, ammonium sulfate was added to the desalted active fraction above (90 ml), absorbed on a Butyl-Toyopearl 650M column (50 ml), which was equilibrated in advance with the buffer containing 30% ammonium sulfate, and washed with 250 ml of the same buffer. Elution with 250 ml of the buffer with a linear gradient from 30% saturated to 0% ammonium sulfate was performed to obtain the active fraction (72 ml). Ammonium sulfate was added to 60% saturation to the active fraction, and it was allowed to stand still for one hour at 0° C., and then centrifuged at 17,500 rpm for 30 minutes. After washing the precipitate with the buffer, the fraction solubilized in 20 ml of the buffer.

(2-5) DEAE-Toyopearl Column Chromatography

Figure 3:
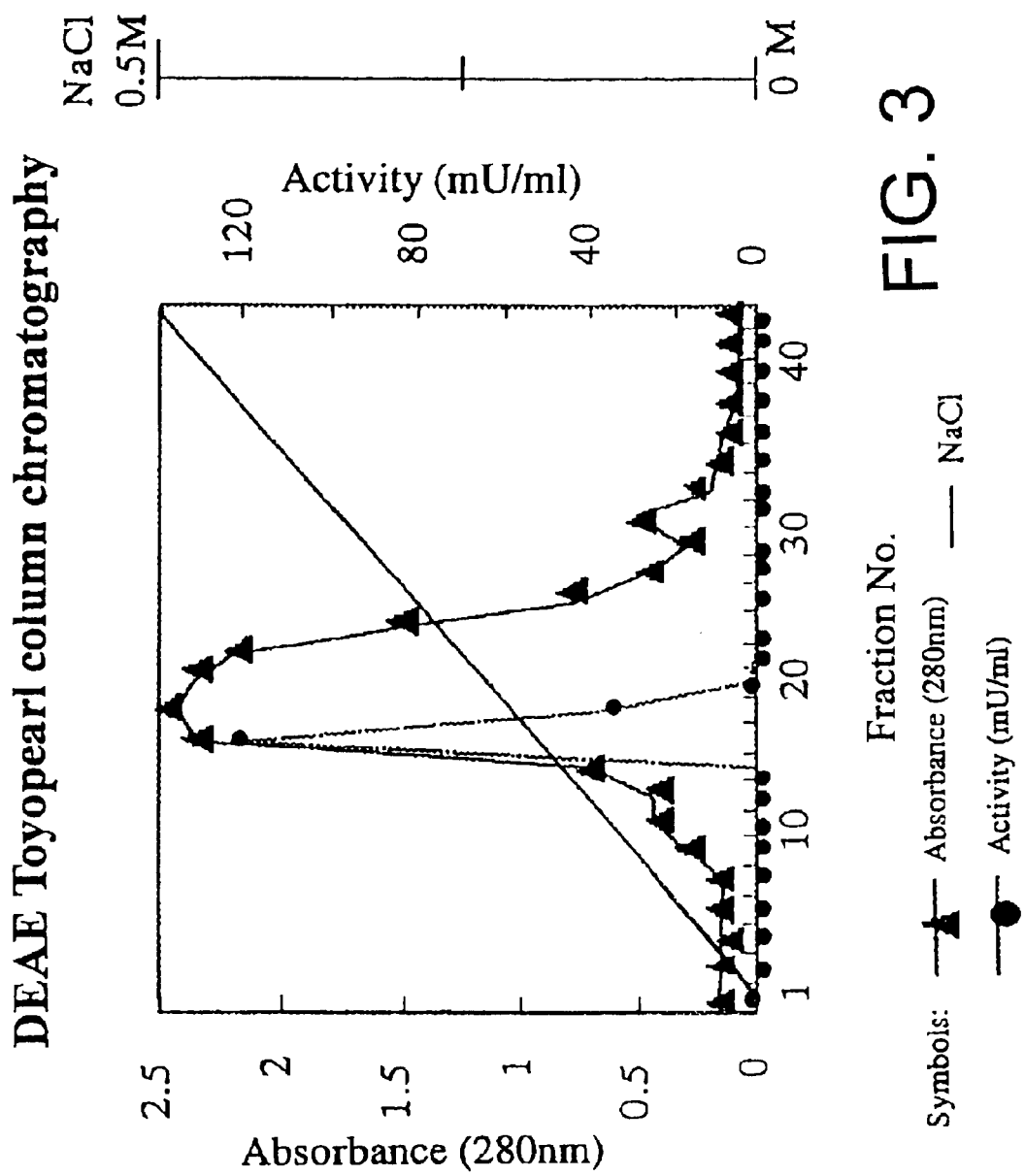
FIG. 3 illustrates purification by DEAE-Toyopearl column chromatography of the D-aminoacylase of the present invention. The triangles denote the absorbance (at 280 nm); the circles the activity (by mU/ml); and the line denotes the concentration of NaCl. Additional parameters include.

The desalted fraction (35 ml) was absorbed on the DEAE-Toyopearl 650M column (50 ml), equilibrated in advance with a buffer, and washed with 200 ml of the same buffer. Elution with 250 ml of the buffer with a linear gradient of 0 to 0.5 M NaCl, the enzyme of the present invention was considered being eluted at a concentration around 0.20 M NaCl, and 5.0 ml of the active fraction was obtained. The result is shown in FIG. 3.

(2-6) HiPrep 16/60 Sephacryl S200 HR Column Chromatography

The present chromatography was conducted at room temperature.

The active fraction obtained above (4.9 ml) was loaded on the HiPrep 16/60 Sephacryl S200 HR, equilibrated in advance with a buffer containing 0.15 M NaCl, eluted with the same buffer and divided into fractions of 1.0 ml. 3 ml of active fraction was obtained. By conducting HiPrep 16/60 Sephacryl S200 column chromatography (FPLC), the active fraction was obtained from the solution by eluting with 48 ml to 52 ml buffer. The activity of the enzyme of the present invention reached the peak at the elution volume of 50.5 ml. (FIG. 4)

The purification process is resumed in Table 1. The enzyme of the present invention was purified 107 folds, from 980 g of wet fungus by various chromatography at a yield of 0.16%. The specific activity was 384 mU/mg.

glycine, 0.1% SDS) was used as the buffer for electrophoresis, and electrophoresis with 30 mA constant current was conducted. The gel was stained with 0.25% Coomassie Brilliant Blue R-250 solution for 1 hour, and was decolorized in a decolorizing solution (methanol:acetic acid:water(25:7.5:67.5) mixture).

By performing SDS-polyacrylamide gel electrophoresis with active fraction after various chromatographies, it was confirmed that the enzyme was purified to a single band with a molecular weight of 40,000 after gel filtration.

TABLE 1

Purification of D-aminoacylase derived from *S. thermonitrificans*

| Purification step | Activity | | | Total protein | Yield | Degree of purification |
|---|---|---|---|---|---|---|
| | (mU) | (mU/ml) | (mU/mg) | (mg) | (%) | (fold) |
| Clude enzyme solution | 24900 | 10.6 | 3.61 | 6900 | 100 | 1 |
| Butyl Toyopearl 650 M (1$^{st}$) | 4230 | 47.0 | 7.25 | 230 | 17 | 2 |
| Butyl Toyopearl 650 M (2$^{nd}$) | 2270 | 64.8 | 24.9 | 14.4 | 9.1 | 3.3 |
| DEAE Toyopearl 650 M | 591 | 121 | 83.8 | 7.06 | 2.4 | 23 |
| Hiprep 16/60 SephacrylS200 | 40.0 | 40.0 | 385 | 0.10 | 0.2 | 107 |

(3) SDS-Polyacrylamide Gel Electrophoresis

| Separation gel solution | |
|---|---|
| 30% acrylamide mix. | 6 ml |
| H$_2$O | 1.3 ml |
| 0.75 M Tris-HCl (pH 8.8) | 7.5 ml |
| 10% SDS | 150 μl |
| TEMED | 12 μl |

50 μl of 25% APS was added to the separation gel solution as prepared above, and after stirring, it was poured into a gel plate until the upper surface of the gel solution reached the line 3 cm below the top of the plate, and H$_2$O was loaded onto the layer. After 10 to 20 minutes, as the gel coagulated, the loaded H$_2$O was discarded.

| Stacking gel solution | |
|---|---|
| 30% acrylamide mix. | 0.75 ml |
| H$_2$O | 2.9 ml |
| 0.75 M Tris-HCl (pH 8.8) | 3.75 ml |
| 10% SDS | 75 μl |
| TEMED | 6 μl |

25 μl of 25% APS was added to the stacking gel solution as prepared above, and after stirring, it was poured into the gel plate to the top, and a comb was inserted. The gel aggregated after about 20 to 60 minutes. A volume of sample treating solution (0.125 M Tris-HCl (pH 6.8), 10% 2-mercaptoethanol, 4% SDS, 10% sucrose, 0.004% Bromophenol Blue) was added to the sample solution, diluted or concentrated as appropriate, treated in boiling water at 100° C. for 3 minutes. And then, applied 20 μl of it onto the gel. Tris-glycine buffer (25 mM Tris-HCl (pH 8.4), 192 mM The yield of the enzyme of the present invention after the purification process was 0.2%, and was purified 107 times, showing a single band by SDS-PAGE.

EXAMPLE 3

Properties of heat-stable D-aminoacylase derived from *Streptomyces thermonitrificans*.

(1) Measurement of the Molecular Weight

The molecular weight was measured by (1) gel filtration method, and (2) SDS-polyacrylamide gel electrophoresis (SDS-PAGE) method.

(1-1) Gel Filtration Method (FIG. 5)

"Superose 12 HR 10/30" (Pharmacia) was used as the column. "Gel Filtration Standard" (Bio-Rad); thyroglobulin (670 K), gamma globulin (158 K), ovalbumin (44 K), myoglobin (17 K), vitamin B-12 (1.35 K) was used as the marker of molecular weight. The flow rate was 0.25 ml/min. As a result, the enzyme of the present invention was determined to have a molecular weight of about 40,000 by gel electrophoresis.

(1-2) SDS-PAGE Method (FIG. 6)

Electrophoresis was conducted according to the method described before using Mini-PROTEAN II electrophoresis apparatus (Bio-Rad) with a constant current of 30 mA. Phosphorylase (97 K), serum albumin (66.1 K), ovalbumin (45 K), carbonic anhydrase (31 K) was used as the marker of molecular weight. After electrophoresis, the gel was stained with Coomassie Brilliant Blue, and compared with the molecular weight marked after decolorizing with decolorizing solution I (100 ml acetic acid, 300 ml methanol, 700 ml pure water) and decolorizing solution II (75 ml acetic acid, 50 ml methanol, 875 ml pure water). As a result, the molecular weight was estimated to be about 40,000.

Thus, the heat-stable D-aminoacylase derived from *Streptomyces thermonitrificans* was estimated to be a monomer with a molecular weight of about 40,000. The molecular weight of the enzyme of the present invention is smaller than that of the D-aminoacylase of genus *Alcaligenes* (MI-4 strain; 51,000, A-6 strain; 52,000, DA1 strain; 55,000, DA181 strain; 58,000), and also was different from that of the D-aminoacylase of genus *Streptomyces* reported before (*S. olivaceus*; 45,000).

(2) Substrate Specificity

The substrate specificity of the enzyme of the present invention was compared taking the enzyme activity against N-acetyl-D-methionine as 100%. N-acetyl-D-valine, N-acetyl-D-phenylalanine, N-acetyl-D-leucine, N-acetyl-D-tryptophan, N-acetyl-D-alanine N-acetyl-L-methionine, N-acetyl-L-leucine, and N-acetyl-L-valine was used as the substrate for comparison. The enzyme activity was measured in a standard reaction solution (total volume of 500 µl containing 100 µl of enzyme solution, and 400 µl of 50 mM Tris/HCl (pH 7.5) containing 20 mM of each substrate and 1 mM cobalt chloride at 30° C. for 60 minutes. The substrate specificity for N-acetyls of D-methionine, D-leucine, D-valine, D-tryptophan, D-alanine and D-phenylalanine is depicted in Table 2.

TABLE 2

Substrate specificity of D-aminoacylase

| Substrate (20 mM) | Activity (mU/ml) | Relative activity (%) |
|---|---|---|
| N-Ac-D-Met | 40.6 | 100 |
| N-Ac-D-Val | 14.7 | 40 |
| N-Ac-D-Leu | 8.93 | 21 |
| N-Ac-D-Ala | 16.9 | 40 |
| N-Ac-D-Trp | 48.4 | 105 |
| N-Ac-D-Phe | 62.2 | 144 |
| N-Ac-L-Met | 0 | 0 |
| N-Ac-L-Val | 0 | 0 |
| N-Ac-L-Phe | 0 | 0 |

The enzyme of the present invention efficiently catalyzes reactions with N-acetyl-D-phenylalanine, N-acetyl-D-tryptophan and N-acetyl-D-methionine, and catalyzes also reactions with N-acetyl-D-leucine, N-acetyl-D-valine and N-acetyl-D-alanine. But didn't catalyze reactions with N-acetyl-L-methionine, N-acetyl-L-phenylalanine and N-acetyl-L-valine.

(3) Properties of the Enzyme (3-1) Thermal Stability of the Enzyme

The enzyme solution was warmed to 30° C. to 70° C. for 30 minutes and was cooled on ice immediately thereafter. Enzyme action of the treated enzyme was measured in 50 mM Tris/HCl (pH 7.5) buffer (total volume of 500 µl) at 30° C. for 60 minutes. The thermal stability of the enzyme of the present invention is shown in FIG. 7. The enzyme of the present invention was comparatively stable until 55° C., however the persistence activity decreased to 20% at 60° C., and was inactivated at 70° C.

(3-2) Optimal Reaction Temperature

Changing only the temperature to one of those selected from 30° C. to 70° C., the enzyme reaction in 50 mM Tris/HCl (pH 7.5) buffer (total volume of 500 µl) for 15 minutes was performed. The optimal reaction temperature of the enzyme of the present invention is shown in FIG. 8. The optimal temperature of the enzyme of the present invention was estimated to be around 60° C.

(3-3) Optimal Reaction pH

Changing only the pH to one of those selected between pH 5.0 to pH 10.0, enzyme reaction at 30° C. for 60 minutes was performed. 50 mM Bis-Tris-HCl buffer was used for the buffer with a pH between pH 5.0 to 7.0, and 50 mM Tris-HCl buffer for that of pH 7.5 to 10.0. The optimal pH of the enzyme of the present invention is shown in FIG. 9. The optimal pH of the enzyme of the present invention was estimated to be around pH 7.0.

(3-4) pH Stability 20 volumes of buffer with a pH between 3 to 11 were added to the enzyme solution. Enzyme reaction at pH 7.5, 30° C. for 60 minutes was performed after incubating for 20 hours at 4° C. 50 mM citrate-NaOH buffer was used for the buffer with pH 5.0 and 3.5, 50 mM Acetate-NaOH buffer for pH 4.0 to 5.0, 50 mM Bis-Tris-HCl buffer for pH 5.0 to 7.0, 50 mM Tris-HCl buffer for pH 7.0 to 10.0, and 50 mM Borate-NaOH buffer for pH 10.0 to 11.0. It was stable around a pH of 7.0. (FIG. 10)

(3-5) Effect of Various Metal Salt and Reagent

Various metal salt and various enzyme inhibitors were added to a concentration of 1 mM to the enzyme reaction, and measurement of the enzyme reaction was performed. The enzyme reaction was conducted in 50 mM Tris/HCl (pH 7.5) buffer (total volume of 500 µl). For the metal salt added reaction, 1 mM of each metal salt or EDTA was added to the standard reaction composition solution without the enzyme and was preincubated at 30° C. for 5 minutes, then enzyme was added to react at 30° C. for 60 minutes. For the enzyme inhibitor added reaction, the standard reaction solution without the substrate was preincubated at 5 minutes, then after adding 1 mM of each inhibitor substrate the substrate was added, and the enzyme reaction was performed at 30° C. for 100 minutes. The relative activity was calculated taking activity of enzyme actions without addition of inhibitors as 100%. The effect of various metal salts and each inhibitor toward the enzyme of the present invention is set forth in Table 3 and Table 4.

TABLE 3

Effect of metal salt for D-aminoacylase

| Metal salt | Activity (mU/ml) | Relative activity (%) |
|---|---|---|
| No addition | 32.1 | 100 |
| $Al_2(SO_4)_2$ | 25.2 | 90 |
| $BaCl_2$ | 30.6 | 95 |
| $CaCl_2$ | 31.1 | 97 |
| $CoCl_2$ | 54.4 | 168 |
| $CuCl_2$ | 1.0 | 3 |
| $FeCl_2$ | 20.4 | 63 |
| $FeCl_3$ | 22.0 | 68 |
| KCl | 30.9 | 93 |
| $MgCl_2$ | 35.2 | 109 |
| $MnCl_2$ | 21.0 | 65 |
| NaCl | 33.1 | 103 |
| $NiCl_2$ | 15.9 | 51 |
| $ZnCl_2$ | 22.2 | 68 |
| $SnCl_2$ | 32.8 | 102 |
| EDTA | 9.4 | 29 |

TABLE 4

Effect of inhibitors against D-aminoacylase

| Reagent | Activity (mU/ml) | Relative activity (%) |
|---|---|---|
| No addition | 45.4 | 100 |
| Hydroxylammonium chloride | 46.5 | 102 |
| KI | 11.3 | 24 |
| Monoiodoacetic acid | 37.9 | 84 |

TABLE 4-continued

Effect of inhibitors against D-aminoacylase

| Reagent | Activity (mU/ml) | Relative activity (%) |
| --- | --- | --- |
| p-Chloromercuribenzoic acid | 2.1 | 4 |
| DTT | 34.8 | 76 |
| N-Ethylmaleimide | 1.3 | 3 |
| NaF | 45.2 | 99 |
| 2,2'-Bipyridyl | 21.9 | 49 |
| 1,5-Diphenylcarbonylhydrazide | 40.5 | 89 |
| Phenylmethylsulfonyl fluoride | 29.5 | 70 |

The activity of the enzyme of the present invention was increased by the addition of 1 mM $Co^{2+}$, but was markedly inhibited by $Cu^{2+}$. Additionally, the enzyme of the present invention was inhibited by SH reagent such as PCMB (p-chloromercuribenzoic acid) and N-ethylmaleimide. Furthermore, it was also inhibited by metal chelating reagent, EDTA.

What is claimed is:

1. A method for producing a D-amino acid comprising contacting a heat-stable D-aminoacylase with an N-acyl-D-amino acid selected from the group consisting of N-acetyl-D-methionine, N-acetyl-D-tryptophan, N-acetyl-D-phenylalanine, N-acetyl-D-valine, N-acetyl-D-alanine, and N-acetyl-D-leucine to produce the corresponding D-amino acid, and recovering said D-amino acid, wherein said D-aminoacylase has the following physicochemical properties:

(a) acts on N-acyl-D-amino acids selected from the group consisting of N-acetyl-D-methionine, N-acetyl-D-tryptophan, N-acetyl-D-phenylalanine, N-acetyl-D-valine, N-acetyl-D-alanine, and N-acetyl-D-leucine to produce the corresponding D-amino acid;

(b) thermal stability such that it is stable at 55° C. when heated at pH 7.5 for 60 minutes and is inactivated at 70° C. or higher under the same condition;

(c) optimal temperature of about 60° C. at pH 7.5;

(d) molecular weight of about 40,000 daltons when determined by SDS-polyacrylamide gel electrophoresis;

(e) optimal pH of about 7.0 at 30° C.;

(f) metal ion effect such that the presence of 1 mM $Co^{2+}$ promotes activity; and (g) metal ion effect such that the presence of 1 mM $Cu^{2+}$ inhibits activity, wherein said D-aminoacylase is derived from a microorganism belonging to the genus *Streptomyces*.

2. A method for producing a D-amino acid comprising contacting a microorganism producing a heat-stable D-aminoacylase with an N-acyl-D-amino acid selected from the group consisting of N-acetyl-D-methionine, N-acetyl-D-tryptophan, N-acetyl-D-phenylalanine, N-acetyl-D-valine, N-acetyl-D-alanine, and N-acetyl-D-leucine to produce the corresponding D-amino acid, and recovering said D-amino acid, wherein said D-aminoacylase has the following physicochemical properties:

(a) acts on N-acyl-D-amino acids selected from the group consisting of N-acetyl-D-methionine, N-acetyl-D-tryptophan, N-acetyl-D-phenylalanine, N-acetyl-D-valine, N-acetyl-D-alanine, and N-acetyl-D-leucine to produce the corresponding D-amino acid;

(b) thermal stability such that it is stable at 55° C. when heated at pH 7.5 for 60 minutes and is inactivated at 70° C. or mere higher under the same condition;

(c) optimal temperature of about 60° C. at pH 7.5;

(d) molecular weight of about 40,000 daltons when determined by SDS-polyacrylamide gel electrophoresis;

(e) optimal pH of about 7.0 at 30° C.;

(f) metal ion effect such that the presence of 1 mM $Co^{2+}$ promotes activity; and (g) metal ion effect such that the presence of 1 mM $Cu^{2+}$ inhibits activity, wherein said D-aminoacylase is derived from a microorganism belonging to the genus *Streptomyces*.

3. The method of claim 1, wherein said microorganism is *Streptomyces thermonitrificans* CS5-9, deposited under the accession number No. FERM BP-7678.

4. The method of claim 1, wherein said D-aminoacylase is a purified enzyme.

5. The method of claim 1, wherein said D-aminoacylase is immobilized on a solid carrier.

6. The method of claim 1, wherein said D-aminoacylase is in the form of a cell free extract of the microorganism.

7. The method of claim 1, wherein said D-aminoacylase is in the form of a cell lysate.

8. The method of claim 2, wherein said microorganism is *Streptomyces thermonitrificans* CS5-9, deposited under the accession number No. FERM BP-7678.

9. The method of claim 2, wherein said microorganism is immobilized on a solid carrier.

10. The method of claim 1, wherein the N-acyl-D-amino acid is present in a mixture with the corresponding N-acyl-L-amino acid.

11. The method of claim 2, wherein the N-acyl-D-amino acid is present in a mixture with the corresponding N-acyl-L-amino acid.

* * * * *

UNITED STATES PATENT AND TRADEMARK OFFICE
CERTIFICATE OF CORRECTION

PATENT NO. : 6,902,915 B2
DATED : June 7, 2005
INVENTOR(S) : Shinji Tokuyama and Akinobu Matsuyama It is certified that error appears in the above-identified patent and that said Letters Patent is hereby corrected as shown below:

Column 24,
Line 16, "C. or mere higher" should read -- C. or higher --.

Signed and Sealed this

Third Day of January, 2006

JON W. DUDAS
*Director of the United States Patent and Trademark Office*